US012616559B2

(12) United States Patent
Ghazvinian Zanjani et al.

(10) Patent No.: US 12,616,559 B2
(45) Date of Patent: May 5, 2026

(54) OBJECT DETECTION AND INSTANCE SEGMENTATION OF 3D POINT CLOUDS BASED ON DEEP LEARNING

(71) Applicant: PROMATON HOLDING B.V., Amsterdam (NL)

(72) Inventors: Farhad Ghazvinian Zanjani, Amsterdam (NL); Teo Cherici, Amsterdam (NL); Frank Theodorus Catharina Claessen, Amsterdam (NL)

(73) Assignee: PROMATON HOLDING B.V., Amsterdam (NL)

( * ) Notice: Subject to any disclaimer, the term of this patent is extended or adjusted under 35 U.S.C. 154(b) by 1053 days.

(21) Appl. No.: 17/626,744

(22) PCT Filed: Jul. 15, 2020

(86) PCT No.: PCT/EP2020/070046
§ 371 (c)(1),
(2) Date: Jan. 12, 2022

(87) PCT Pub. No.: WO2021/009258
PCT Pub. Date: Jan. 21, 2021

(65) Prior Publication Data
US 2023/0186476 A1 Jun. 15, 2023

(30) Foreign Application Priority Data

Jul. 15, 2019 (EP) ..................................... 19186357

(51) Int. Cl.
*A61C 9/00* (2006.01)
*A61B 5/00* (2006.01)
(Continued)

(52) U.S. Cl.
CPC ........... *A61C 9/0053* (2013.01); *G06N 3/045* (2023.01); *G06N 3/0464* (2023.01); *G06T 7/10* (2017.01);
(Continued)

(58) Field of Classification Search
CPC .... A61C 9/0053; G06N 3/045; G06N 3/0464; G06N 3/084; G06T 7/10; G06T 7/62;
(Continued)

(56) References Cited

U.S. PATENT DOCUMENTS 6,721,387 B1 4/2004 Naidu et al.
7,987,099 B2 7/2011 Kuo et al.
(Continued)

FOREIGN PATENT DOCUMENTS

CN 101977564 A 2/2011
CN 106618760 A 5/2017
(Continued)

OTHER PUBLICATIONS

Zanjani et al (NPL "Deep Learning Approach to Semantic Segmentation in 3D Point Cloud Intra-Oral Scans of Teeth" Published 2019 by MIDL 2019—Full paper track Total 15 pages (Year: 2019).*
(Continued)

*Primary Examiner* — Quoc A Tran
(74) *Attorney, Agent, or Firm* — Steven M. Koehler; Westman, Champlin & Koehler, P.A.

(57) ABSTRACT

A method of object detection in a point cloud includes: determining first features associated with points of a point cloud representing one or more objects in at least a 3D space and defining geometrical information for each point of the point cloud, a first type of network being configured to receive points of the point cloud as input; determining second point cloud features based on the first features, the second features defining local geometrical information
(Continued)

about the point cloud at positions of nodes of a uniform 3D grid; generating an object, an object proposal defining a 3D bounding box, the 3D bounding box that may define an object; and determining, by a third type of deep neural network, a score for a 3D anchor indicating a probability that the 3D anchor, the determining being based on second features that are located in the 3D anchor.

18 Claims, 15 Drawing Sheets

(51) Int. Cl.

| | |
|---|---|
| *G06F 18/2413* | (2023.01) |
| *G06F 18/2415* | (2023.01) |
| *G06N 3/045* | (2023.01) |
| *G06N 3/0464* | (2023.01) |
| *G06N 3/084* | (2023.01) |
| *G06T 7/10* | (2017.01) |
| *G06T 7/62* | (2017.01) |
| *G06V 10/25* | (2022.01) |
| *G06V 10/44* | (2022.01) |
| *G06V 10/764* | (2022.01) |
| *G06V 10/82* | (2022.01) |
| *G06V 20/64* | (2022.01) |

(52) U.S. Cl.
CPC ............... *G06T 7/62* (2017.01); *G06V 10/25* (2022.01); *G06V 10/454* (2022.01); *G06V 10/764* (2022.01); *G06V 10/82* (2022.01); *G06V 20/64* (2022.01); *A61B 5/0088* (2013.01); *G06F 18/24133* (2023.01); *G06F 18/2415* (2023.01); *G06N 3/084* (2013.01); *G06T 2207/10028* (2013.01); *G06T 2207/20021* (2013.01); *G06T 2207/20081* (2013.01); *G06T 2207/20084* (2013.01); *G06T 2207/30036* (2013.01)

(58) Field of Classification Search
CPC . G06T 2207/10028; G06T 2207/20021; G06T 2207/20081; G06T 2207/20084; G06T 2207/30036; G06V 10/25; G06V 10/454; G06V 10/764; G06V 10/82; G06V 20/64; A61B 5/0088; G06F 18/24133; G06F 18/2415
See application file for complete search history.

(56) References Cited

U.S. PATENT DOCUMENTS

| | | | |
|---|---|---|---|
| 8,099,305 | B2 | 1/2012 | Kuo et al. |
| 8,135,569 | B2 | 3/2012 | Matov et al. |
| 8,439,672 | B2 | 5/2013 | Matov et al. |
| 8,639,477 | B2 | 1/2014 | Cheinokov et al. |
| 9,107,722 | B2 | 8/2015 | Matov et al. |
| 9,135,498 | B2 | 9/2015 | Andreiko et al. |
| 9,904,999 | B2 | 2/2018 | Andreiko et al. |
| 10,032,271 | B2 | 7/2018 | Somasundaram et al. |
| 10,235,606 | B2 | 3/2019 | Miao et al. |
| 10,456,229 | B2 | 10/2019 | Fisker et al. |
| 10,610,185 | B2 | 4/2020 | Taguchi et al. |
| 10,685,259 | B2 | 6/2020 | Salah et al. |
| 10,932,890 | B1 | 3/2021 | Sant et al. |
| 10,997,727 | B2 | 5/2021 | Xue et al. |
| 11,007,036 | B2 | 5/2021 | Pokotilov et al. |
| 11,107,218 | B2 | 8/2021 | Salah et al. |
| 2005/0019732 | A1 | 1/2005 | Kaufmann et al. |
| 2005/0192835 | A1 | 9/2005 | Kuo et al. |
| 2008/0085487 | A1 | 4/2008 | Kuo et al. |
| 2008/0253635 | A1 | 10/2008 | Spies et al. |

| | | | |
|---|---|---|---|
| 2009/0191503 | A1 | 7/2009 | Matov et al. |
| 2010/0069741 | A1 | 3/2010 | Kuhn et al. |
| 2011/0038516 | A1 | 2/2011 | Koehler et al. |
| 2011/0081071 | A1 | 4/2011 | Benson et al. |
| 2011/0255765 | A1 | 10/2011 | Carlson et al. |
| 2012/0063655 | A1 | 3/2012 | Dean et al. |
| 2013/0022251 | A1 | 1/2013 | Chen et al. |
| 2013/0039556 | A1 | 2/2013 | Kachelriess et al. |
| 2013/0230818 | A1 | 9/2013 | Matov et al. |
| 2014/0169648 | A1 | 6/2014 | Andreiko et al. |
| 2014/0227655 | A1 | 8/2014 | Andreiko et al. |
| 2015/0029178 | A1 | 1/2015 | Claus et al. |
| 2016/0008095 | A1 | 1/2016 | Matov et al. |
| 2016/0034788 | A1 | 2/2016 | Lin et al. |
| 2016/0042509 | A1 | 2/2016 | Andreiko et al. |
| 2016/0078647 | A1 | 3/2016 | Schildkraut et al. |
| 2016/0117850 | A1 | 4/2016 | Jin et al. |
| 2016/0324499 | A1 | 11/2016 | Sen Sharma et al. |
| 2016/0371862 | A1 | 12/2016 | Silver et al. |
| 2017/0024634 | A1 | 1/2017 | Miao et al. |
| 2017/0046616 | A1 | 2/2017 | Socher et al. |
| 2017/0100212 | A1 | 4/2017 | Sherwood et al. |
| 2017/0150937 | A1 | 6/2017 | Stille et al. |
| 2017/0169562 | A1 | 6/2017 | Somasundaram et al. |
| 2017/0265977 | A1 | 9/2017 | Fisker et al. |
| 2017/0270687 | A1 | 9/2017 | Manhart |
| 2018/0005377 | A1 | 1/2018 | Alvarez et al. |
| 2018/0028294 | A1 | 2/2018 | Azernikov et al. |
| 2018/0110590 | A1 | 4/2018 | Maraj et al. |
| 2018/0182098 | A1 | 6/2018 | Andreiko et al. |
| 2018/0253866 | A1 | 9/2018 | Jain et al. |
| 2018/0300877 | A1 | 10/2018 | Somasundaram et al. |
| 2019/0026599 | A1 | 1/2019 | Salah et al. |
| 2019/0147245 | A1 | 5/2019 | Qi et al. |
| 2019/0147666 | A1 | 5/2019 | Keustermans et al. |
| 2019/0148005 | A1 | 5/2019 | Domracheva et al. |
| 2019/0164288 | A1 | 5/2019 | Wang et al. |
| 2019/0172200 | A1 | 6/2019 | Andreiko et al. |
| 2019/0282333 | A1 | 9/2019 | Matov et al. |
| 2019/0328489 | A1 | 10/2019 | Capron-Richard et al. |
| 2020/0015948 | A1 | 1/2020 | Fisker et al. |
| 2020/0022790 | A1 | 1/2020 | Fisker |
| 2020/0085535 | A1 | 3/2020 | Pokotilov et al. |
| 2020/0179089 | A1 | 6/2020 | Serval et al. |
| 2020/0320685 | A1 | 10/2020 | Anssari Moin et al. |
| 2021/0045843 | A1 | 2/2021 | Pokotilov et al. |
| 2021/0082184 | A1 | 3/2021 | Claessen et al. |
| 2021/0110584 | A1 | 4/2021 | Claessen et al. |
| 2021/0150702 | A1 | 5/2021 | Claessen et al. |
| 2021/0174543 | A1 | 6/2021 | Claessen et al. |
| 2021/0217233 | A1 | 7/2021 | Feng et al. |
| 2021/0264611 | A1 | 8/2021 | Xue et al. |
| 2021/0322136 | A1 | 10/2021 | Anssari Moin et al. |
| 2022/0067943 | A1 | 3/2022 | Claessen et al. |
| 2023/0263605 | A1 | 8/2023 | Madden et al. |

FOREIGN PATENT DOCUMENTS

| | | |
|---|---|---|
| CN | 108205806 A | 6/2018 |
| CN | 108305684 A | 7/2018 |
| CN | 111316285 A | 6/2020 |
| EP | 2742857 A1 | 6/2014 |
| EP | 3121789 A1 | 1/2017 |
| EP | 3462373 A1 | 4/2019 |
| EP | 3591616 A1 | 1/2020 |
| EP | 3671531 A1 | 6/2020 |
| EP | 3767521 A1 | 1/2021 |
| JP | 2007-525289 A | 9/2007 |
| JP | 2010-220742 A | 10/2010 |
| JP | 2013-537445 A | 10/2013 |
| JP | 2017-102622 A | 6/2017 |
| JP | 2017-520292 A | 7/2017 |
| JP | 2017-157138 A | 9/2017 |
| JP | 2019159940 A | 9/2019 |
| JP | 2022-501299 A | 1/2022 |
| WO | 2015169910 A1 | 11/2015 |
| WO | 2016143022 A1 | 9/2016 |
| WO | 2017099990 A1 | 6/2017 |
| WO | 2019002616 A1 | 1/2019 |

(56) References Cited

FOREIGN PATENT DOCUMENTS

| WO | 2019002631 A1 | 1/2019 |
|---|---|---|
| WO | 2019068741 A2 | 4/2019 |
| WO | 2019122373 A1 | 6/2019 |
| WO | 2019207144 A1 | 10/2019 |
| WO | 2020007941 A1 | 1/2020 |
| WO | 2020048960 A1 | 3/2020 |
| WO | 2020127398 A1 | 6/2020 |

OTHER PUBLICATIONS

Hossein et al (NPL "Prediction of myocardial infarction by assessing regional cardiac wall in CMR images through active mesh modeling" Published 2018 by Computers in Biology and Medicine Total 9 pages (Year: 2017).*

Office Action in corresponding Japanese application No. 2022-501299 dated Mar. 18, 2024.

Atzmon et al. "Point Convolutional Neural Networks by Extension Operators", Mar. 27, 2018, 14 pages, arXiv:1803.10091v1 [cs.CV].

Hamida et al. "Deep Learning for Semantic Segmentation of Remote Sensing Images with Rich Spectral Content", 2017 IEEE International Geoscience and Remote Sensing Symposium (IGARSS), 2017, pp. 2569-2572.

Schulze et al. "Artefacts in CBCT: A Review", Dentomaxillofacial Radiology, Jul. 1, 2011, pp. 265-273, vol. 40, No. 5.

Sekuboyina et al. "A Localisation-Segmentation Approach for Multi-Label Annotation of Lumbar Vertebrae Using Deep Nuts", Cornell University Library, 201 Olin Library Cornell University Ithaca, NY 14853, Mar. 13, 2017, 10 pages.

Silva et al. "Automatic Segmenting Teeth in X-Ray Images: Trends, a Novel Data Set, Benchmarking and Future Perspectives", Feb. 9, 2018, 33 pages, retrieved online from https://arxiv.org/pdf/1802.03086.pdf.

Simonovsky et al. "A Deep Metric for Multimodal Registration" International Conference on Medical Image Computing and Computer-Assisted Intervention (MICCAI), 2016, pp. 10-18, vol. 9902.

Skrodzki et al. "Directional Density Measure to Intrinsically Estimate and Counteract Non-Uniformity in Point Clouds", Computer Aided Geometric Design, Aug. 2018, pp. 73-89, vol. 64.

Shaoqing et al. "Mask R-CNN", Proceedings of the IEEE International Conference on Computer Vision, 2017, pp. 2961-2969.

Szegedy et al. "Going Deeper With Convolutions", 2015 IEEE Conference on Computer Vision and Pattern Recognition (CVPR), Jun. 2015, pp. 1-9.

Tian, S. "Automatic Classification and Segmentation of Teeth on 3D Dental Model Using Hierarchical Deep Learning Networks" IEEE Journals & Magazine, Jun. 21, 2019, pp. 84817-84828.

Tonioni et al. "Learning to Detect Good 3D Keypoints", International Journal of Computer Vision, 2018, pp. 1-20, vol. 126.

Wang et al. "Dynamic Graph CNN for Learning on Point Clouds", ACM Trans. Graph, Jan. 2019, vol. 1, No. 1, 13 pages.

Wang et al. "SGPN: Similarity Group Proposal Network for 3D Point Cloud Instance Segmentation", CVF Conference on Computer Vision and Pattern Recognition, Nov. 23, 2017, 13 pages.

Wu et al. "Tooth Segmentation on Dental Meshes Using Morphologic Skeleton", Computers & Graphics, Feb. 2014, pp. 199-211, vol. 38.

Wu et al. "3D ShapeNets: A Deep Representation for Volumetric Shapes", 2015 IEEE Conference on Computer Vision and Pattern Recognition (CVPR), 2015, pp. 1912-1920.

Wu et al. "Model-Based Teeth Reconstruction", ACM Transactions on Graphics (TOG), ACM, US, Nov. 11, 2016, pp. 1-13, vol. 35, No. 6.

Xu et al. "SpiderCNN: Deep Learning on Point Sets with Parameterized Convolutional Filters", Computer Vision—EECV, 2018, 16 pages.

Yau et al. "Tooth Model Reconstruction Based Upon Data Fusion for Orthodontic Treatment Simulation", Computers in Biology and Medicine, May 1, 2014, pp. 8-16, vol. 48.

Yi et al. "GSPN: Generative Shape Proposal Network for 3D Instance Segmentation in Point Cloud", Proceedings of the IEEE/CVF Conference on Computer Vision and Pattern Recognition (CVPR), 2019, 13 pages.

Yu, Y. "Machine Learning for Dental Image Analysis", Nov. 2016, 61 pages, https://arxiv.org/ftp/arxiv/papers/1611/1611.09958.pdf, retrieved Nov. 30, 2017.

Zhang, Y. and Yu, H. "Convolutional Neural Network Based Metal Artifact Reduction in X-Ray Computed Tomography", IEEE Transactions on Medical Imaging, Jun. 2018, pp. 1370-1381, vol. 37, No. 6.

Zhang, C. and Xing, Y. "CT Artifact Reduction via U-Net CNN", SPIE, Medical Imaging 2018: Image Processing, Mar. 2, 2018, 6 pages, vol. 10574.

Zhou et al. "A Method for Tooth Model Reconstruction Based on Integration of Multimodal Images", Journal of Healthcare Engineering, Jun. 20, 2018, vol. 8, pp. 1-8.

International Search Report and Written Opinion for corresponding International Application No. PCT/EP2020/070046 dated Sep. 3, 2020.

Non-published U.S. Appl. No. 17/415,465, filed Jun. 17, 2021.

Kamnitsas et al. "Efficient Multi-scale 3D CNN With Fully Connected CRF for Accurate Brain Lesion Segmentation", Medical Image Analysis, 2017, pp. 61-78, vol. 36.

Ahn, B. "The Compact 3D Convolutional Neural Network for Medical Images", Jul. 2, 2017, pp. 1-9, http://cs231n.standord.edu/reports/2017/pdfs/23/pdf, retrieved Dec. 18, 2018.

Auro Tripathy, "Five Insights from GoogLeNet You Could Use in Your Own Deep Learning Nets", Sep. 20, 2016, pp. 1-21, https://www.slideshare.net/aurot/googlenet-insights?from_action=save, retrieved Dec. 18, 2018.

Bustos et al. "An Experimental Comparison of Feature-Based 3D Retrieval Methods" 2nd International Symposium on 3D Data Processing, Visualization, and Transmission, 3DPVT 2004, Sep. 6-9, 2004, pp. 215-222.

Chaouch, M. and Verroust-Blondet, A. "Alignment of 3D Models", Graphical Models, Mar. 2009, pp. 63-76, vol. 71, No. 2.

Chen et al. "Deep RBFNet: Point Cloud Feature Learning Using Radial Basis Functions", Cornell University Library, Dec. 11, 2018, 11 pages.

Chen et al. "Fast Resampling of 3D Point Clouds via Graphs", IEEE Transactions on Signal Processing, Feb. 1, 2018, pp. 666-681, vol. 66, No. 3.

Çiçek et al. "3D U-Net: Learning Dense Volumetric Segmentation from Sparse Annotation", Medical Image Computing and Computer-Assisted Intervention—MICCAI 2016, Part II, Oct. 2, 2016, pp. 424-432.

Duda et al. "Pattern Classification: Introduction", 2001, Pattern Classification, New York, John Wiley & Sons, US, pp. 1-13.

Duy et al. "Automatic Detection and Classification of Teeth in CT Data", International Conference on Medical Image Computing and Computer-Assisted Intervention—MICCAI 2012, 2012, pp. 609-616.

Eun, H. and Kim, C. "Oriented Tooth Localization for Periapical Dental X-ray Images via Convolutional Neural Network", Asia-Pacific Signal and Information Processing Association Annual Summit and Conference (APSIPA), Dec. 3, 2016, pp. 1-7.

Everingham et al. "The Pascal Visual Object Classes (VOC) Challenge", International Journal of Computer Vision, Sep. 9, 2009, pp. 303-338, vol. 88, No. 2.

Fang et al. "3D Deep Shape Descriptor", 2015 IEEE Conference on Computer Vision and Pattern Recognition (CVPR), 2015, pp. 2319-2328.

Fechter et al. "A 3D Fully Convolutional Neural Network and a Random Walker to Segment the Esophagus in CT", Apr. 21, 2017, 23 pages, https://arxiv.org/pdf/1704.06544.pdf, retrieved Dec. 18, 2018.

Ghafoorian et al. "EL-GAN: Embedding Loss Driven Generative Adversarial Networks for Lane Detection", Computer Vision—ECCV 2018 Workshops, Jan. 23, 2019, pp. 256-272, vol. 11129.

Ghazvinian Zanjani et al. "Deep Learning Approach to Semantic Segmentation in 3D Point Cloud Intra-oral Scans of Teeth", Proceedings of the 2nd International Conference on Medical Imaging

(56) References Cited

OTHER PUBLICATIONS with Deep Learning, 2019, 22 pages, retrieved online from https://openreview.net/forum?id=ByxLSoblgV.

Gkantidis et al. "Evaluation of 3-Dimensional Superimposition Techniques on Various Skeletal Structures of the Head Using Surface Models", PLOS ONE, Feb. 23, 2015, 20 pages, vol. 10, No. 2.

Gjesteby et al. "Deep Learning Methods for CT Image-Domain Metal Artifact Reduction", SPIE, Developments in X-Ray Tomography XI, Sep. 25, 2017, 6 pages, vol. 10391.

Gomes et al. "Efficient 3D Object Recognition Using Foveated Point Clouds", Computers & Graphics, May 1, 2013, pp. 496-508, vol. 37.

Gorler, O. and Akkoyun, S. "Artificial Neural Networks Can be Used as Alternative Method to Estimate Loss Tooth Root Sizes for Prediction of Dental Implants", Cumhuriyet University Faculty of Science Science Journal (CSJ), Apr. 2017, pp. 385-395, vol. 38, No. 2.

Guo et al. "3D Mesh Labeling via Deep Convolutional Neural Networks", ACM Transactions on Graphics, Dec. 2015, pp. 1-12, vol. 35, No. 1, Article 3.

Hall, P. and Owen, M. "Simple Canonical Views", Proceedings of the British Machine Vision Conference (BMVC), Sep. 2005, 10 pages.

Han et al. "Deep Residual Learning for Compressed Sensing CT Reconstruction via Persistent Homology Analysis", Cornell University Library, Nov. 19, 2016, pp. 1-10.

He et al. "Deep Residual Learning for Image Recognition", 2016 IEEE Conference on Computer Vision and Pattern Recognition (CPR), Jun. 2016, pp. 770-778.

Hermosilla et al. "Monte Carlo Convolution for Learning on Non-Uniformly Shaped Point Clouds", ACM Transactions on Graphics, Nov. 2018, 12 pages, vol. 37, No. 6, Article 235.

Hongming Li, Y. "Non-Rigid Image Registration Using Fully Convolutional Networks With Deep Self-Supervision", Sep. 3, 2017, 8 pages.

Hou et al. "3D-SIS: 3D Semantic Instance Segmentation of RGB-D Scans", Computer Vision and Pattern Recognition (CPR), Apr. 29, 2019, 14 pages.

Huang et al. "Edge-Aware Point Set Resampling", ACM Transactions on Graphics, 2013, pp. 1-12, vol. 32, No. 1, Article 9.

Isola et al. "Image-to-Image Translation with Conditional Adversarial Networks", 2017 IEEE Conference on Computer Vision and Pattern Recognition (CVPR), Honolulu, HI, 2017, pp. 5967-5976.

Joda, T. and Gallucci, G. "Systematic Literature Review of Digital Three-Dimensional Superimposition Techniques to Create Virtual Dental Patients", The International Journal of Oral & Maxillofacial Implants, 2015, pp. 330-337, vol. 30, No. 2.

Johari et al. "Detection of Vertical Root Fractures in Intact and Endodontically Treated Premolar Teeth by Designing a Probabilistic Neural Network: An ex vivo Study", Dentomaxillofacial Radiology, Feb. 2017, vol. 46, No. 2, pp. 1-9.

Jung et al. "Combining Volumetric Dental CT and Optical Scan Data for Teeth Modeling", Computer-Aided Design, Oct. 2015, pp. 24-37, vol. 67-68.

Klinder et al. "Automated Model-Based Vertebra Detection, Identification, and Segmentation in CT Images", Medical Image Analysis, Jun. 2009, pp. 471-482, vol. 13, No. 3.

Ku et al. "Joint 3D Proposal Generation and Object Detection from View Aggregation", IEEE/RSJ International Conference on Intelligent Robots and Systems (IROS), Jul. 12, 2018, pp. 1-8.

Le T. and Duan Y. "PointGrid: A Deep Network for 3D Shape Understanding", Proceedings of the IEEE Conference on Computer Vision and Pattern Recognition, Jun. 18-23, 2018, pp. 9204-9214.

Li et al. "PointCNN: Convolution on X-Transformed Points", Neural Information Processing Systems (NIPS), Nov. 5, 2018, 11 pages.

Li et al. "SO-Net: Self-Organizing Network for Point Cloud Analysis", Eye In-Painting with Exemplar Generative Adversarial Networks, Jun. 2018, pp. 9397-9406.

Liao et al. "Automatic Tooth Segmentation of Dental Mesh Based on Harmonic Fields", Biomedical Research International, 2015, 10 pages, vol. 2015.

Litjens et al. "A Survey on Deep Learning in Medical Image Analysis", Medical Image Analysis, Dec. 2017, pp. 60-88, vol. 42.

Liu, C. and Furukawa, Y. "MASC: Multi-scale Affinity with Sparse Convolution for 3D Instance Segmentation", Computer Vision and Pattern Recognition (CPR), Feb. 12, 2019, 4 pages.

Meyer et al. "Normalized Metal Artifact Reduction (NMAR) in Computed Tomography", Medical Physics, Oct. 2010, pp. 5482-5493, vol. 37, No. 10.

Miki et al. "Classification of Teeth in Cone-Beam CT Using Deep Convolutional Neural Network", Computers in Biology and Medicine, Jan. 2017, pp. 24-29, vol. 1, No. 80.

Miki et al. "Tooth Labeling in Cone-Beam CT Using Deep Convolutional Neural Network for Forensic Identification", SPIE 10134, Medical Imaging 2017: Computer-Aided Diagnosis, Mar. 3, 2017, 6 pages.

Pavaloiu et al. "Automatic Segmentation for 3D Dental Reconstruction", IEEE 6th ICCCNT, Jul. 13-15, 2015.

Pavaloiu et al. "Neural Network Based Edge Detection for CBCT Segmentation", 5th IEEE EHB, Nov. 19-21, 2015.

Qi et al. "Frustum PointNets for 3D Object Detection from RGB-D Data", Computer Vision and Pattern Recognition (CPR), Apr. 13, 2018, 15 pages.

Qi et al. "PointNet++: Deep Hierarchical Feature Learning on Point Sets in a Metric Space", Conference on Neural Information Processing Systems (NIPS), Jun. 2017, 14 pages.

Qi et al. "PointNet: Deep Learning on Point Sets for 3D Classification and Segmentation", Computer Vision and Pattern Recognition (CVPR), 2017, 19 pages.

Ravanbakhsh et al. "Deep Learning With Sets and Point Clouds", Feb. 24, 2017, 12 pages, retrieved online from https://arxiv.org/abs/1611.04500.

Ruellas et al. "3D Mandibular Superimposition: Comparison of Regions of Reference for Voxel-Based Registration" PLOS ONE, Jun. 23, 2016, 13 pages.

Ryu et al. "Analysis of Skin Movement With Respect to Flexional Bone Motion Using MR Images of a Hand", Journal of Biomechanics, 2006, pp. 844-852, vol. 39, No. 5.

Gutierrez-Becker et al. "Learning Optimization Updates for Multimodal Registration", Medical Image Computing and Computer-Assisted Intervention—MICCAI 2016, 2016, pp. 19-27.

Hosntalab et al. "A Hybrid Segmentation Framework for Computer-Assisted Dental Procedures", IEICE Transactions on Information and Systems, Oct. 2009, pp. 2137-2151, vol. E92D, No. 10.

Studholme et al. "Automated Three-Dimensional Registration of Magnetic Resonance and Positron Emission Tomography Brain Images by Multiresolution Optimization of Voxel Similarity Measures", Medical Physics, 1997, pp. 25-35, vol. 24. No. 1.

Office Action in corresponding Canadian patent application serial No. 3, 146,240 dated Jul. 30, 2025.

* cited by examiner

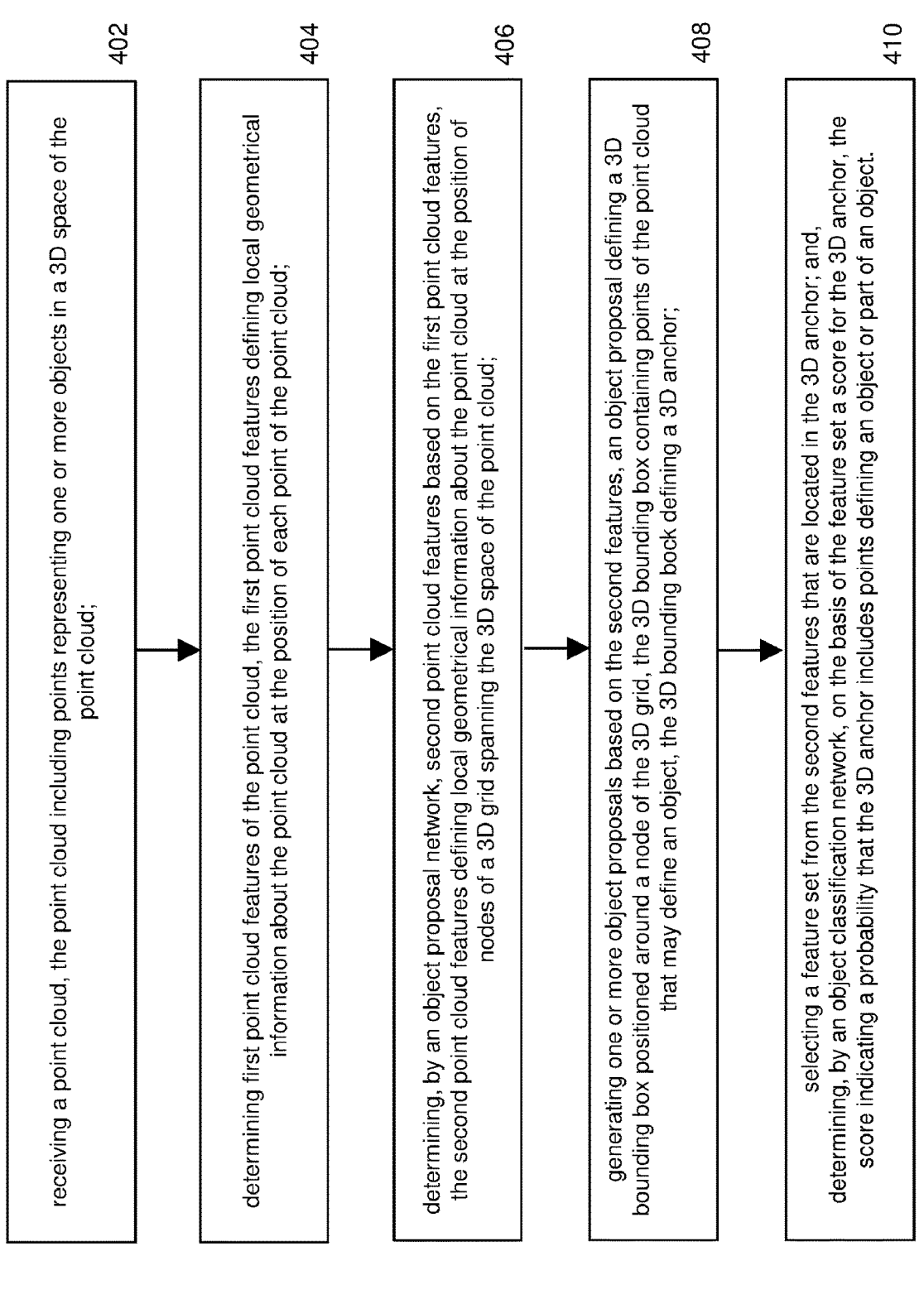

402 receiving a point cloud, the point cloud including points representing one or more objects in a 3D space of the point cloud;

404 determining first point cloud features of the point cloud, the first point cloud features defining local geometrical information about the point cloud at the position of each point of the point cloud;

406 determining, by an object proposal network, second point cloud features based on the first point cloud features, the second point cloud features defining local geometrical information about the point cloud at the position of nodes of a 3D grid spanning the 3D space of the point cloud;

408 generating one or more object proposals based on the second features, an object proposal defining a 3D bounding box positioned around a node of the 3D grid, the 3D bounding box containing points of the point cloud that may define an object, the 3D bounding bock defining a 3D anchor;

410 selecting a feature set from the second features that are located in the 3D anchor; and, determining, by an object classification network, on the basis of the feature set a score for the 3D anchor, the score indicating a probability that the 3D anchor includes points defining an object or part of an object.

FIG. 4A

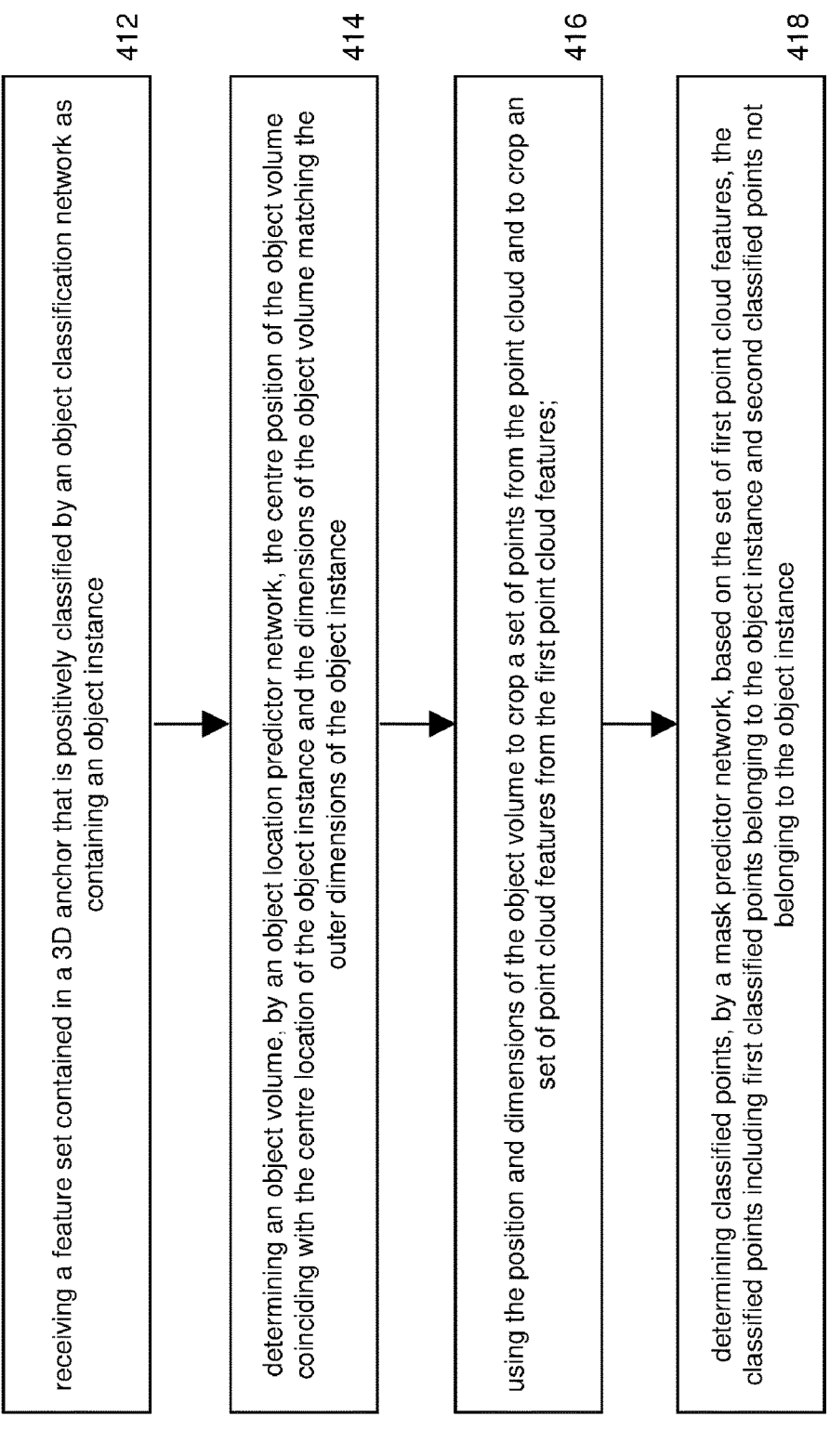

receiving a feature set contained in a 3D anchor that is positively classified by an object classification network as containing an object instance — 412 determining an object volume, by an object location predictor network, the centre position of the object volume coinciding with the centre location of the object instance and the dimensions of the object volume matching the outer dimensions of the object instance — 414 using the position and dimensions of the object volume to crop a set of points from the point cloud and to crop an set of point cloud features from the first point cloud features; — 416 determining classified points, by a mask predictor network, based on the set of first point cloud features, the classified points including first classified points belonging to the object instance and second classified points not belonging to the object instance — 418

FIG. 4B

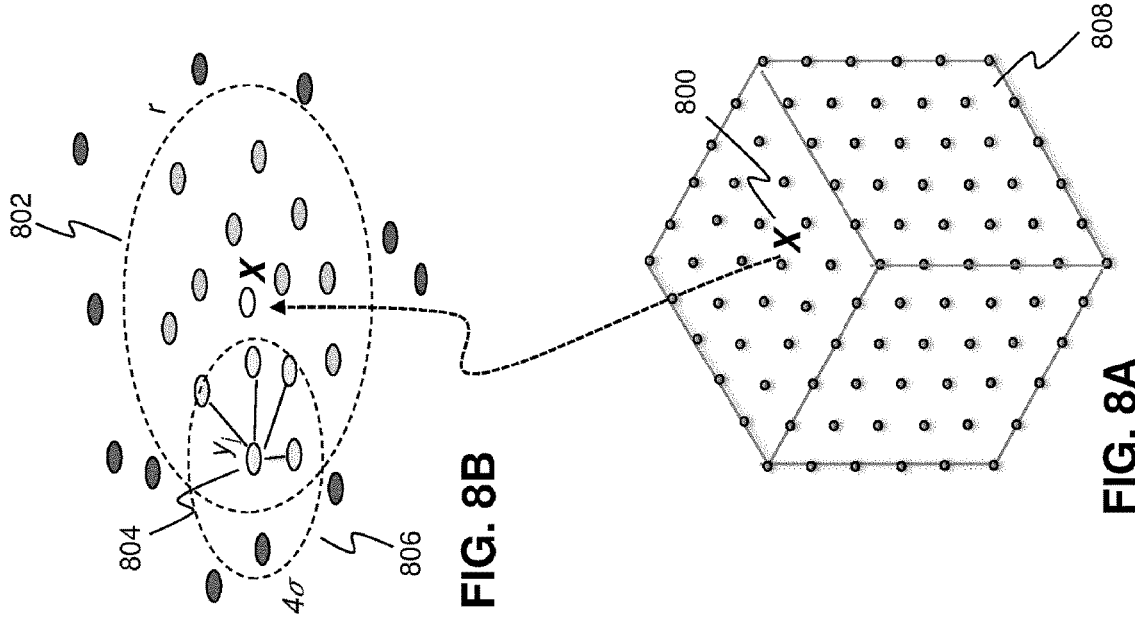
FIG. 8A
FIG. 8B
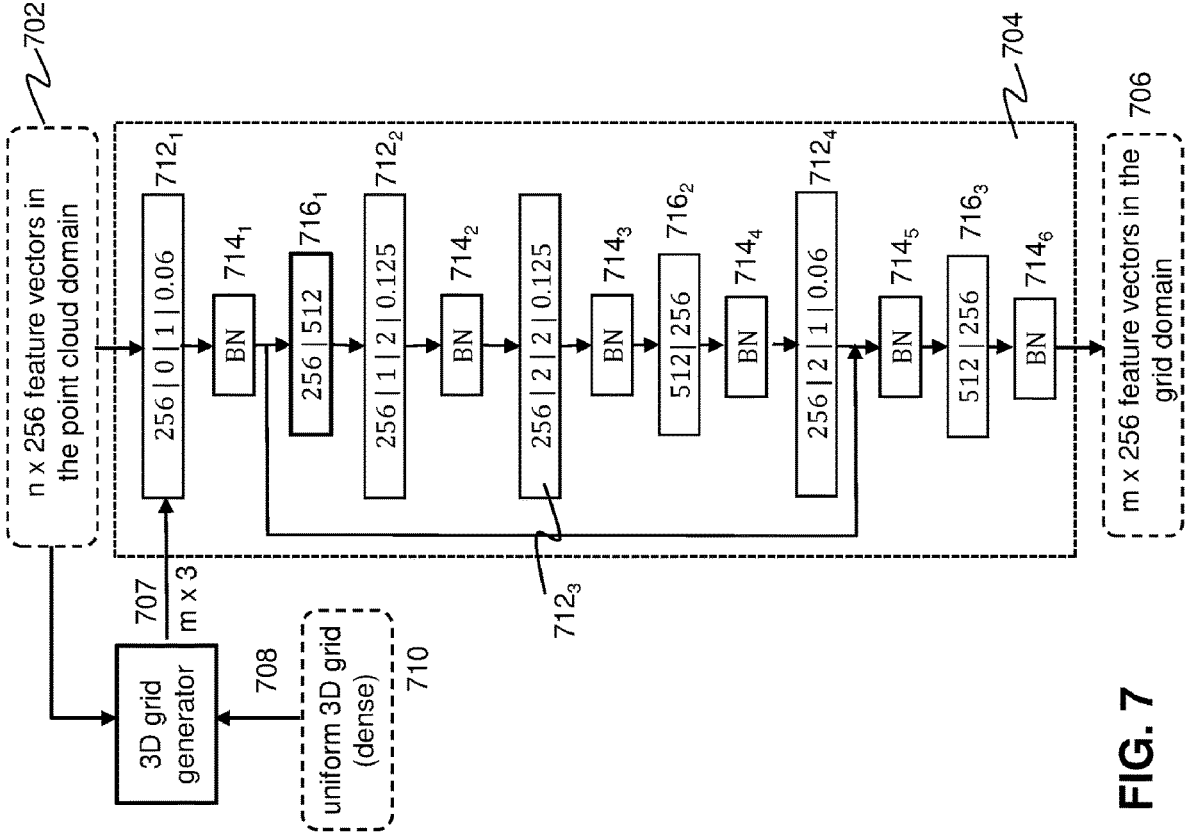
FIG. 7

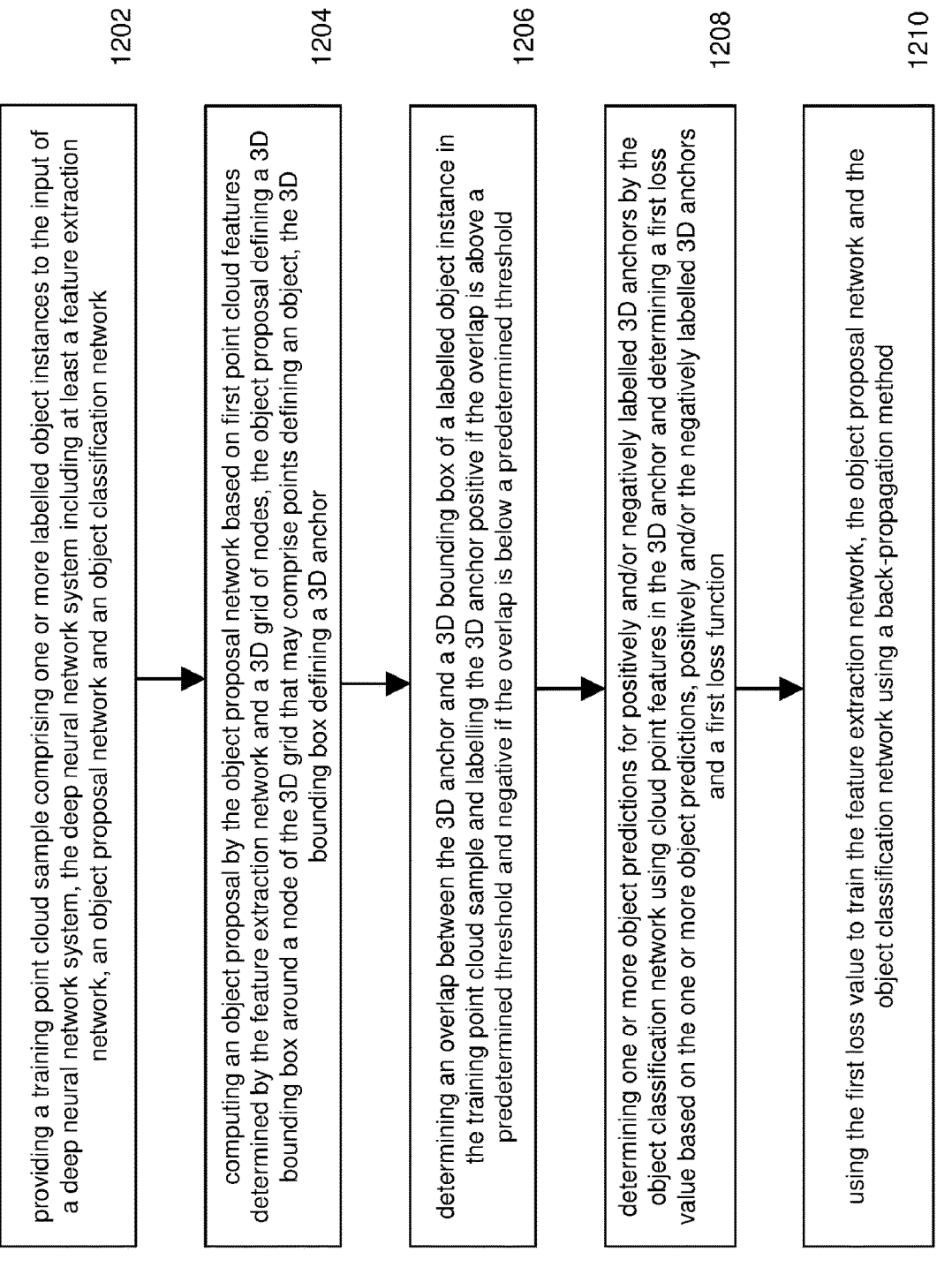

providing a training point cloud sample comprising one or more labelled object instances to the input of a deep neural network system, the deep neural network system including at least a feature extraction network, an object proposal network and an object classification network

1202 computing an object proposal by the object proposal network based on first point cloud features determined by the feature extraction network and a 3D grid of nodes, the object proposal defining a 3D bounding box around a node of the 3D grid that may comprise points defining an object, the 3D bounding box defining a 3D anchor

1204 determining an overlap between the 3D anchor and a 3D bounding box of a labelled object instance in the training point cloud sample and labelling the 3D anchor positive if the overlap is above a predetermined threshold and negative if the overlap is below a predetermined threshold

1206 determining one or more object predictions for positively and/or negatively labelled 3D anchors by the object classification network using cloud point features in the 3D anchor and determining a first loss value based on the one or more object predictions, positively and/or the negatively labelled 3D anchors and a first loss function

1208 using the first loss value to train the feature extraction network, the object proposal network and the object classification network using a back-propagation method

1210

FIG. 12A providing a training point cloud sample comprising one or more labelled object instances to the input of a deep neural network system, the deep neural network system including at least a feature extraction network, an object proposal network, an object classification network, an object location predictor network and a mask predictor network — 1222 computing an object proposal by the object proposal network based on first point cloud features determined by the feature extraction network and a 3D grid of nodes, the object proposal defining a 3D bounding box around a node of the 3D grid that may comprise points defining an object, the 3D bounding box defining a 3D anchor — 1224 determining an overlap between the 3D anchor and a 3D bounding box of a labelled object instance in the training point cloud sample and labelling the 3D anchor positive if the overlap is above a predetermined threshold and negative if the overlap is below a predetermined threshold — 1226 determining one or more object predictions for positively and/or negatively labelled 3D anchors by the object classification network using cloud point features in the 3D anchor and determining a first loss value based on the one or more object predictions, positively and/or the negatively labelled 3D anchors and a first loss function — 1228 determining a location and size prediction of an object volume, by the object location predictor network, based on features in the 3D anchor, and using the location and size prediction and a second loss function to determine a second loss contribution — 1230 determining classified points, by the mask predictor network, based on point cloud features in the object volume, the classified points including first classified points belonging to the object instance and second classified points not belonging to the object instance, and using the classified points and a third function to determine a third loss contribution — 1232 using the first, second and third loss contributions to train the feature extraction network, the object proposal network, the object classification network, the object location predictor network and the mask predictor network using a back-propagation method — 1234

OBJECT DETECTION AND INSTANCE SEGMENTATION OF 3D POINT CLOUDS BASED ON DEEP LEARNING

CROSS-REFERENCE TO RELATED APPLICATION(S)

This Application is a Section 371 National Stage Application of International Application No. PCT/EP2020/070046, filed Jul. 15, 2020, and published as WO 2021/009258 A1 on Jan. 21, 2021, and further claims priority to European Patent Application No. 19186357.0, filed Jul. 15, 2019.

FIELD OF THE INVENTION

The invention relates to object detection and instance segmentation of 3D point clouds based on deep learning, and in particular, though not exclusively, to methods and systems for object detection in 3D point clouds using deep learning, to methods and system for instance segmentation of 3D point clouds using deep learning, a deep neural network system for object detection in 3D point clouds, a deep neural network system for instance segmentation of 3D point clouds and a computer program product for executing such methods.

BACKGROUND OF THE INVENTION

In image processing instance segmentation refers to the process of object detection wherein specific objects in an image are detected (typically by determining bounding boxes comprising each of the detected objects) and creating a pixel mask for each identified object. Instance segmentation can be thought as object detection where the output is a pixel mask instead of just a bounding box. Thus, unlike semantic segmentation, which aims to categorize each pixel in an image, instance segmentation aims to label pixels in determined bounding boxes. Recently, fast and reliable instance segmentation for 2D camera images based on a so-called Mask R-CNN deep learning scheme is seeing increasing application in solving real-world problems. However, in many applications such as autonomous driving, robotics and certain medical applications, the sensor information that needs to be analyzed represents a 3D scene, not a 2D scene. These 3D applications rely on information generated by optical scanners, e.g. laser scanners such as LiDAR used in surveying applications and intra-oral scanners used in dentistry, which typically generate non-uniform 3D volumetric data in the form of a point cloud. These data are not structured in the form of a homogenous grid of data such as pixels or—case of non-optical 3D scanners, e.g. CT scanners—voxels.

Data acquisition schemes based on optical scanners typically generate 3D volumetric data in the form of a point cloud data set or—in short—a point cloud. Data points of a point cloud may represent the surface of objects. Typically, point clouds include a large number of points which are non-uniformly distributed in the 3D space. The 3D space may include areas of densely distributed data points, areas of sparsely distributed data points and areas that do not have data points at all, e.g. the void space 'inside' objects. The term point cloud may refer any type 3D data set wherein each point may be represented as a vector in a 3D space. The points may be associated with further attributes, e.g. color or the like. Special types of point clouds include 3D surface definitions such as triangle meshes or polygon meshes.

Although 3D analysis based on a point cloud is a rapidly growing field of technology, schemes for 3D object detection and instance segmentation are still in their infancy when compared to their 2D counterparts. Currently only few sources are known that address 3D instance segmentation, Qi, et al describe in their article "Frustum pointnets for 3D object detection from RGB-D data" IEEE Conference on Computer Vision and Pattern Recognition. pp. 918-927 (2018) a hybrid framework involving two stages wherein in a first stage 2D bounding boxes of objects are detected in 2D images and in a second stage a 3D point cloud is processed in a 3D search space, partially bound by the 2D bounding boxes. Similarly, Hou, et al. describe in their article "3D-SIS: 3D semantic instance segmentation of RGB-D scans". arXiv preprint arXiv:1812.07003 (2018) a model wherein first 2D images are processed by a 2D convolutional network. Thereafter, the learned features are back-projected on a voxelized point cloud data, where the extracted 2D features and the geometric information are combined to obtain object proposals and per-voxel mask prediction. The dependency of the above-described models on 2D image(s) and voxelization limits the performance of such approaches.

In another approach, Yi, et al described in their article "Generative shape proposal network for 3d instance segmentation in point cloud", arXiv preprint arXiv:1812.03320 (2018) an analysis-by-synthesis strategy wherein instead of directly determining object bounding boxes in a point cloud, a conditional variational auto-encoder (CVAE) is used. However, GSPN training requires a rather complex separate two-stage training of the CVAE part and the region-based networks (which perform the classification, regression and mask generation on the proposals).

In yet another approach, object proposals are determined based on a clustering scheme. Wang, et al described in their article "Similarity group proposal network for 3d point cloud instance segmentation", IEEE Conference on Computer Vision and Pattern Recognition. pp. 2569-2578 (2018) the use of a similarity matrix between the features of each pair of points in the embedded feature space, to indicate whether the given pair of points belong to the same object instance or not. However, computing such a pair-wise distance is impractical for large point clouds. Similarly, Liu et al describe in their article "Masc: Multi-scale affinity with sparse convolution for 3D instance segmentation", arXiv preprint arXiv:1902.04478 (2019) voxelization of the point cloud for processing the volumetric data by a 3D U-Net model and a clustering scheme to find similarities between each pair of points by comparing their extracted features in several hidden layers of a trained U-Net. Vaxelization and similarity computations for large fine-detailed point cloud greatly limits the performance of such approaches.

Hence, from the above it follows that there is a need in the art for improved instance segmentation of 3D point cloud. In particular, there is a need for methods and system that enable accurate, fast and computation efficient instance segmentation of 3D point clouds.

SUMMARY OF THE INVENTION

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Functions described in this disclosure may be implemented as an algorithm executed by a microprocessor of a computer. Furthermore, aspects of the present invention may take the form of a computer program product embodied in one or more computer readable medium(s) having computer readable program code embodied, e.g., stored, thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber, cable, RF, etc., or any suitable combination of the foregoing. Computer program code for carrying out operations for aspects of the present invention may be written in any combination of one or more programming languages, including a functional or an object oriented programming language such as Java™, Scala, C++, Python or the like and conventional procedural programming languages, such as the "C" programming language or similar programming languages. The program code may execute entirely on theme user's computer, partly on the user's computer, as a stand-alone software package, partly on the user's computer and partly on a remote computer, or entirely on the remote computer, server or virtualized server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor, in particular a microprocessor or central processing unit (CPU), or graphics processing unit (GPU), of a general purpose computer, special purpose computer, or other programmable data processing apparatus to produce a machine, such that the instructions, which execute via the processor of the computer, other programmable data processing apparatus, or other devices create means for implementing the functions/acts specified in the flowchart and/or block diagram block or blocks. For example, and without limitation, illustrative types of hardware logic components that may be used include Field-Programmable Gate Arrays (FPGAs), Application-specific Integrated Circuits (ASICs), Application-Specific Standard Products (ASSPs), System-on-a-Chip systems (SOCs), Complex Programmable Logic Devices (CPLDs), etc.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function (s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts, or combinations of special purpose hardware and computer instructions.

In this application, methods and systems for object detection and instance segmentation scheme for a 3D point cloud are described. A point cloud represents a data set which at least defines the geometrical positions of points (such as Cartesian coordinates of points) in the point cloud. Additionally, in some embodiments, the points may be associated with other attributes, e.g. color or normal vector, as well. Therefore, a point of a point cloud may define a vector of information, including at least a position in a 3D space. Point clouds can be generated by scanning a predetermined object using a 3D optical scanner. Such object could for example be a dento-maxillofacial structure, wherein the lento-max-illofacial structure may include a dentition comprising teeth.

In an aspect, the invention relates to a method of object detection in a point cloud, preferably a point cloud generated by an 3D optical scanner such as an intra-oral scanning (IOS) point cloud, wherein the method may comprise: determining by a first type of neural network first features associated with points of a point cloud, the point cloud including points representing one or more objects in at least a 3D space of the point cloud, the first features defining geometrical information for each point of the point cloud, the first type of network being configured to receive points of the point cloud as input; determining, by a second type of deep neural network, second features based on the first features, the second features defining local geometrical information about the point cloud at the positions of nodes of a uniform 3D grid, the nodes being uniformly distributed in the 3D space of the point cloud; determining one or more object proposals based on the second features, an object proposal defining a 3D bounding box positioned around a node of the 3D grid, the 3D bounding box containing points of the point cloud that may define an object, the 3D bounding box defining a 3D anchor; and, determining, by a third type of deep neural network, a score for the 3D anchor, the score indicating a probability that the 3D anchor includes points defining an object or part of an object, the determining being based on second features that are located in the 3D anchor.

The method provides an accurate and efficient way to detect objects in a point cloud. The process is directly applied to the point cloud (the input data) so that all geometrical information embedded in the point cloud can be used for object detection. Furthermore, the process determines objects in a point cloud by evaluation of features in a new domain, the grid domain, without the need to classify each point in the point cloud. This way, the process provides a very efficient way of detecting (predicting) if points representing a predetermined object are present in a point cloud.

In an embodiment, the second type of deep neural network may also be trained to determine a score for nodes of the uniform 3D grid, the score indicating a probability that the 3D anchor includes points defining an object or part of an object. In an embodiment, the first point cloud features may include first feature vectors, each first feature vector being associated with a point of the point cloud; and/or, the second point cloud features may include second feature vectors, each second feature vector being associated with a node of the uniform 3D grid.

In an embodiment, the first point cloud features may be determined by a first type of deep neural network, the first type of deep neural network defining a feature extraction network.

In an embodiment, the first type of network may be configured to receive points of the point cloud and to generate the first features, preferably first feature vectors associated with the points of the point cloud.

In an embodiment, the first type of deep neural network may include a plurality of convolutional layers including multilayer perceptrons (MLPs), the feature extraction network being configured to receive points of a point cloud at its input and to generate a feature vector for each point of the point cloud at its output.

In an embodiment, the feature extraction network may include one or more $\chi$-Conv layers, each $\chi$-Conn layer being configured to weigh and permute points and corresponding features provided to the input of the $\chi$-Conv layer and subsequently subjecting the permuted points and features to a convolution kernel, preferably the feature extraction network being configured as PointCNN, comprising $\chi$-Conv layers.

In an embodiment, the second type of deep neural network may represent an object proposal network, the object proposal network including a plurality of convolutional layers, each of the plurality of convolutional layers including a multilayer perceptron (MLP) including one or more convolutional kernels.

In an embodiment, at least one of the plurality of convolutional layers may be configured to receive the first features and nodes of the uniform 3D grid and to determine the second features based on the first features.

In an embodiment, the uniform 3D grid may be determined based on the spatial distribution of points in the 3D space of the point cloud.

In an embodiment, the object proposal network may be configured as a Monte Carlo Convolutional Network (MCCNet), comprising a plurality of Monte Carlo (MC) spatial convolutional layers, preferably a MC spatial convolutional layer comprising a convolutional kernel configured for determining a convolution at a location of a node x located in the 3D space of the point cloud.

In an embodiment, the determining a convolution including: determine neighboring points y within the receptive field r, the receptive field defining the field of view (FOV) of the convolutional kernel; determine for each neighboring point y a probability density function p(x,y); determine the convolution at a node based on a Monte Carlo estimation using the neighboring points y and the probability density value p(x,y) for each neighboring point.

In an embodiment, the third type of deep neural network may represent an object classification network, the third type of deep neural network including a plurality of fully connected (FC) multilayer perceptron (MLP) layers, the second type of deep neural network being configured to receive features associated with a 3D anchor and to use the features to determine a score associated with the 3D anchor, the score indicating a probability that the 3D anchor includes points defining an object or part of an object.

In an aspect, the invention may relate to a computer system adapted to object detection in a point cloud, preferably point cloud generated by an 3D optical scanner such as an intra-oral scanning (iOS) point cloud, comprising:

a computer readable storage medium having computer readable program code embodied therewith, the program code including a pre-processing algorithm and at least a trained first 3D deep neural network, the computer readable program code; and a processor, preferably a microprocessor, coupled to the computer readable storage medium, wherein responsive to executing the first computer readable program code, the processor is configured to perform executable operations comprising: determining by a first type of neural network first features associated with points of a point cloud, the point cloud including points representing one or more objects in a 3D space of the point cloud, the first features defining geometrical information for each point of the point cloud, the first type of network being configured to receive points of the point cloud as input; determining, by a second type of deep neural network, second features based on the first features, the second features defining local geometrical information about the point cloud at the position of nodes of a uniform 3D grid, the nodes being uniformly distributed in the 3D space of the point cloud; determining one or more object proposals based on the second features, an object proposal defining a 3D bounding box positioned around a node of the uniform 3D grid, the 3D bounding box containing points of the point cloud that may define an object, the 3D bounding bock defining a 3D anchor; and, determining, by a second third of deep neural network, a score for the 3D anchor, the score indicating a probability that the 3D anchor includes points defining an object or part of an object, the determining being based on second features that are located in the 3D anchor.

In an aspect, the invention may relate to a computer system adapted for instance segmentation of a point cloud, preferably a point cloud generated by an 3D optical scanner such as an intra-oral scanning (IOS) point cloud, comprising: a computer readable storage medium having computer readable program code embodied therewith, the program code including a pre-processing algorithm and at least a trained first 3D deep neural network, the computer readable program code; and a processor, preferably a microprocessor, coupled to the computer readable storage medium, wherein responsive to executing the first computer readable program code, the processor is configured to perform executable operations comprising: determining by a first type of deep neural network first features associated with points of a point cloud, the point cloud including points representing one or more objects in a 3D space of the point cloud, the first features defining geometrical information for each point of the point cloud, the first type of network being configured to receive points of the point cloud as input; determining, by a second type of deep neural network, second features, the second features defining local geometrical information about the point cloud at the position of nodes of a uniform 3D grid, the nodes being uniformly distributed in the 3D space of the point cloud; determining object proposals based on the second features, an object proposal defining a 3D volume containing points that may define an object, the 3D volume of an object proposal defining a 3D anchor positioned around a node of the 3D grid; determining a classified 3D anchor, by a third type of deep neural network, the determining being based on a second feature set, the second feature set being a subset of the second features that are located in the 3D anchor; determining an object volume, by a fourth type of deep neural network (object location predictor network), a center position of the object volume coinciding with a center location of the object instance and the dimensions of the object volume matching the outer dimensions of the object instance, the determining being based the second feature set; and, determining classified points, by a fifth type of deep neural network (mask predictor network), based on a set of points and a set of first point cloud features that are located in the object volume, the classified points including first classified points belonging to the object instance and second classified points not belonging to the object instance.

In another aspect, the invention may relate to a method of training a deep neural network system for object detection in a point cloud, preferably an intra-oral scanning (IOS) point cloud, the method comprising: providing a training point cloud sample comprising one or more labelled object instances to the input of the deep neural network system, the deep neural network system including at least a feature extraction network, an object proposal network and an object classification network; computing an object proposal based on second features, the second features defining local geometrical information about the point cloud at the position of nodes of a uniform 3D grid, the nodes being uniformly distributed in the 3D space of the point cloud, the second features being determined by the object proposal network, wherein the object proposal network is configured to determine the second features based on first features generated by the feature extraction network which receives the training point cloud sample at its input, the object proposal defining a 3D bounding box around a node of the uniform 3D grid that may comprise points defining an object, the 3D bounding box defining a 3D anchor; determining an overlap between the 3D anchor and a 3D bounding box of a labelled object instance in the training point cloud sample and labelling the 3D anchor positive if the overlap is above a predetermined threshold and negative if the overlap is below a predetermined threshold; determining one or more object predictions for positively and/or negatively labelled 3D anchors by the object classification network using cloud point features in the 3D anchor and determining a first loss value based on the one or more object predictions, positively and/or the negatively labelled 3D anchors and a first loss function; and, using the first loss value to train the feature extraction network, the object proposal network and the object classification network concurrently using a back-propagation method.

In yet another aspect, the invention may relate to a method of training a deep neural network system for instance segmentation of a point cloud, preferably a point cloud generated by an 3D optical scanner such as an intra-oral scanning (IOS) point cloud, the method comprising: providing a training point cloud sample comprising one or more labelled object instances to the input of a deep neural network system, the deep neural network system including at least a feature extraction network, an object proposal network, an object classification network, an object location predictor network and a mask predictor network; computing an object proposal based on second features, the second features defining local geometrical information about the point cloud at the position of nodes of a uniform 3D grid, the nodes being uniformly distributed in the 3D space of the point cloud, the second features being determined by the object proposal network, wherein the object proposal network is configured to determine the second features based on first features generated by the feature extraction network which receives the training point cloud sample at its input, the object proposal defining a 3D bounding box defining a 3D anchor; determining an overlap between the 3D anchor and a 3D bounding box of a labelled object instance in the training point cloud sample and determining a positive 3D anchor if the overlap is above a predetermined threshold and a negative 3D anchor if the overlap is below a predetermined threshold; determining one or more object predictions for positively and negatively labelled 3D anchors by the object classification network using cloud point features in the 3D anchor and determining a first loss value based on the one or more object predictions and a first loss function; determining a location and size prediction of an object volume, by the object location predictor network, based on features in the 3D anchor, and using the location and size prediction and a second loss function to determine a second loss contribution; determining classified points, by the mask predictor network, based on point cloud features in the object volume, the classified points including first classified points belonging to the object instance and second classified points not belonging to the object instance, and using the classified points and a third function to determine a third loss contribution; and, using the first, second and third loss contributions to train the feature extraction network, the object proposal network, the object classification network, the object location predictor network and the mask predictor network using, preferably concurrently using, a back-propagation method. The first point cloud features and second 3D grid features may be implicitly learned concurrently through the process of training of the system of neural networks.

The methods and systems described in this application are based on an object detection and instance segmentation model (scheme), which may be referred to as the Mask-MCNet. The Mask-MCNet allows accurate and efficient object detection and instance segmentation in a 3D point cloud, for example intra-oral scanning (IDS) data generated by an intra-oral scanner. In contrast with known deep learning models, the model does not require a voxelization step for processing a point cloud. Consequently, the data can be processed while preserving fine-detail geometrical information of the point cloud, which is important for a successful segmentation of detailed structures. Furthermore, by the extraction and transformation of first point cloud features into second point cloud features on a uniform 3D grid, the Mask-MCNet can efficiently handle the processing of highly non-uniform point cloud data, resulting in fast generation of object proposals in a point cloud. Such property is important for the scalability of the scheme to large-sized point cloud data structures (e.g. more than 100k points). Experimental results show that the Mask-MCNet achieves a 98% IoU (intersection of union) score on the test data, thereby outperforming the state-of-the-art networks in a point cloud segmentation task. The performance of the Mask-MCNet is close to the human level and complete point cloud object detection and segmentation can be obtained in only a few seconds of processing time, while being a lengthy and labor intensive task for a human.

In certain embodiments, the system may comprise three modules wherein each module may include one or several subnetworks. The first module (feature extraction) may comprise a deep neural network that is trained to transform the geometrical position of input point set into the high-dimensional feature space. The thus obtained high-dimensional feature vector for each point, may be transferred to a 3D grid which spans in the whole 3D space. Such a transformation is performed by the second module (object proposal) that may include a Monte-Carlo convolutional network or another suitable network architecture. This network may be trained to distribute and transform information contained in the feature vector of each point of the irregular point cloud, (as obtained from the first module) to a regular grid domain. For detecting whether there is an object (e.g. tooth) inside each candidate bounding box (also referred to as an anchor) a third module may be employed which may comprise two subnetworks. All features on the node of grid, which are encompassed by the candidate anchor are examined by the classification subnetwork for detecting anchors that have high-degree of overlap with the objects in the 3D space. In case of positively detected anchor by the classification subnetwork, another subnet (object location predictor network) is used for estimating the difference values of candidate anchor bounding box and the center of the object in the candidate anchor bounding box, compared with their ground truth. After localizing each object, the mask generator network which may consist of an MLP-based cascade network is employed for a binary classification of all points from the input point cloud inside the detected bounding box. Such a classification task aims for finding the points which belong to each object encompassed completely by the detected bounding box. Thus, the model is capable of first detecting all objects in the input point cloud by fitting a 3D bounding box centralized at the center of each object and secondly indicates all the points that belong to each individual tooth inside each detected bounding box.

It is submitted that while the embodiments in this application identify and describe (functionally) separate network components, such as separate deep learning networks, alternatively in other embodiments combinations of these separate network components may be considered a single connected network. The invention will be further illustrated with reference to the attached drawings, which schematically will show embodiments according to the invention. It will be understood that the invention is not in any way restricted to these specific embodiments.

BRIEF DESCRIPTION OF THE DRAWINGS

FIGS. 4A and 4B depict flow-diagrams of processes for object detection and instance segmentation of a point cloud according to various embodiments of the invention.

FIG. 7 depicts a schematic of an object proposal network according to an embodiment of the invention.

FIGS. 8A and 8B depict schematics of part of a Monte Carlo convolutional network according to an embodiment of the invention.

FIGS. 12A and 12B depict flow-diagrams of training deep learning systems according to various embodiments of the invention.

DETAILED DESCRIPTION

The embodiments described in this disclosure include systems and computer-implemented methods for accurate and efficient object detection and instance segmentation of irregular (non-uniform) 3D point clouds based on one or more deep neural networks (DNNs). A point cloud may refer to a set of sampling points defining a 3D representation of one or more objects or a scene including one or more objects. Each sampling point (in short point) may be represented by a vector in a 3D Cartesian coordinate system which is not universal (i.e. the Cartesian coordinate system can be different between two IOS data sets). A point cloud may be structured as 3D surface meshes wherein points in the 3D space may define triangle or polygon meshes, which collectively describe a surface mesh in a 3D space. A normal vector associated with a the meshes may define an orientation in the 3D space. A normal vector associated with each point in the point cloud may represent a vector perpendicular to the surface comprised of each point and its neighbors. In contrast to Euclidean 2D and 3D data sets such as pixel and voxel representations, point clouds are irregular, permutation-invariant and may have a variable number of points per scan. In this application, the term point cloud is used to refer to any non-Euclidean 3D data set for representing an object in 3D space based on points in a 3D space.

Figure 1:
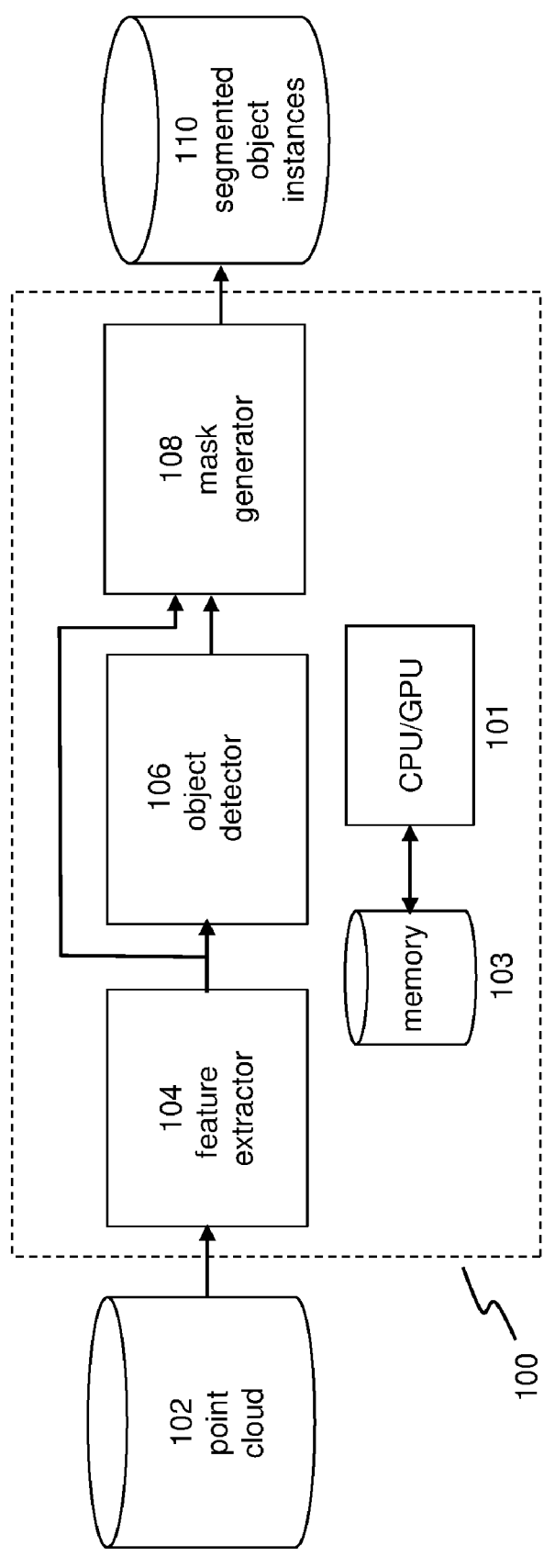
FIG. 1 is an illustration of a deep learning system for object detection and instance segmentation of 3D point clouds according to an embodiment of the invention.

FIG. 1 depict a schematic of a deep learning system for object detection and instance segmentation of point cloud according to an embodiment of the invention. In particular, FIG. 1 depicts a system 100 for instance segmentation of 3D point clouds. The process of object detection and instance segmentation of a 3D point cloud by the system is schematically depicted in FIG. 2A-2D. The system may be implemented on one or more computers comprising one or more processing units 101 connected to memory 103. The system may be configured to execute a plurality of units, including 3D deep neural networks that may be trained to receive (part(s) of) a point cloud and, optionally, spatial information associated with the point cloud at their input, and process the data according to a trained model. The system may be implemented as a stand-alone system (e.g. a server system or a network application such as a cloud application) connected to data storage and retrieval system, e.g. a database system or the like, including one or more storage units e.g. databases.

Figures 2A, 2B, 2C, 2D:
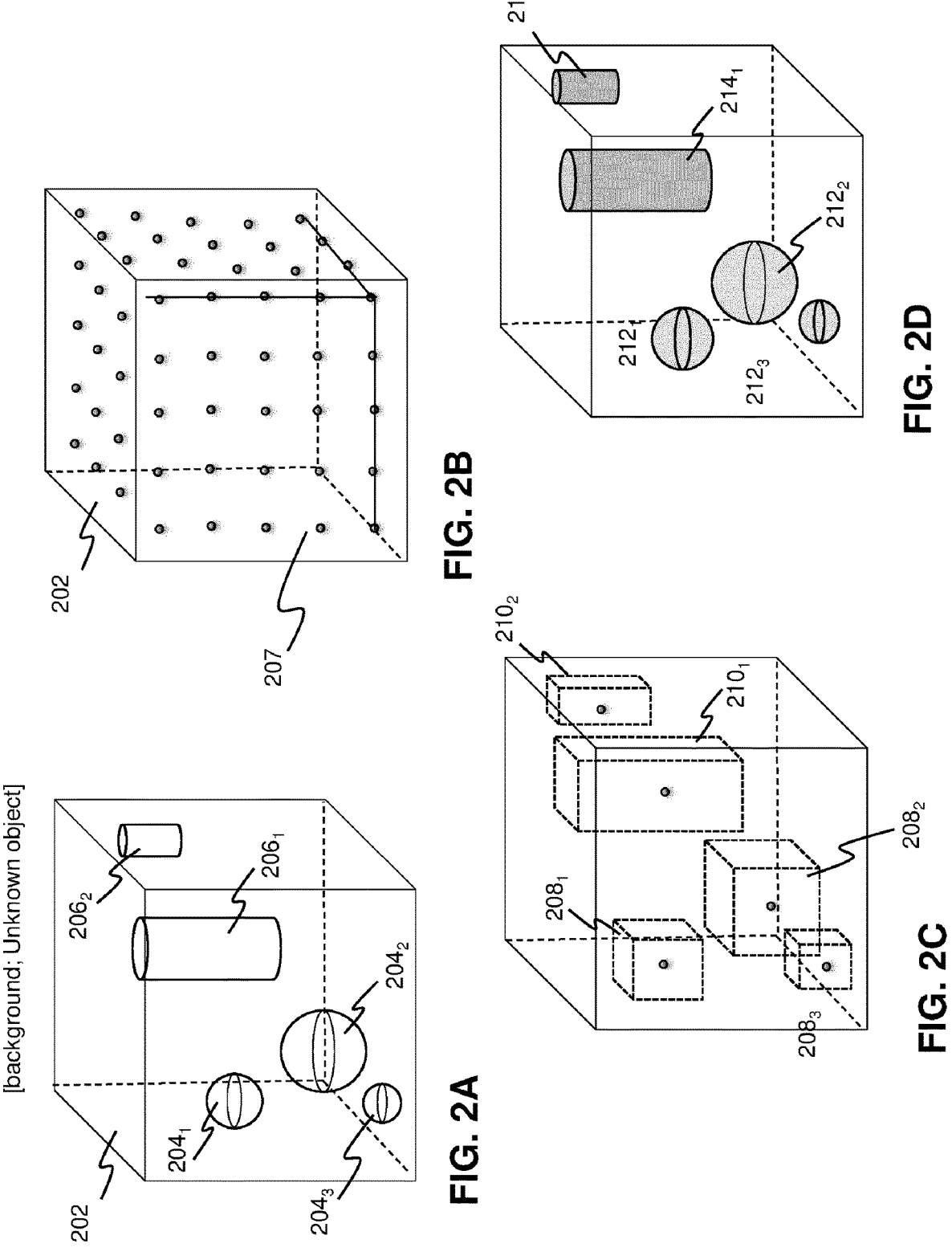
FIG. 2A-2D depicts a scheme for object detection and instance segmentation of 3D point clouds according to an embodiment of the invention.

As shown in FIG. 1, the deep learning system may include a plurality of units, including at least a feature extractor 104, an object detector 106 and a mask generator 108. The feature extractor may include a first deep neural network configured to receive an irregular 3D point cloud 102 at its input. A schematic of a point cloud representation is depicted in FIG. 2A. The point cloud may include an irregular set of points representing at least part of a surface of one or more (different) objects, e.g. first objects representing spheres $204_{1-3}$ and/or second objects $206_{1,2}$ representing cylinders. Typically, the points may be represented as coordinates, e.g. Cartesian coordinates x,y,z, in a 3D space 202. The first deep neural network may be configured to determine a feature vector for each point of the point cloud. In an embodiment, the features may be formatted as a feature vector, i.e. a multi-element vector (in the example 256 elements). A feature vector associated with a point may describe spatial correlations between the point and other points in the 3D point cloud, typically other points that are located within a certain distance from the point. The feature vectors may be used by the object detector and the mask generator to efficiently perform instance segmentation of objects in the point cloud.

The object detector 106 may include a deep neural network system configured to generate object proposals. An object proposal may include a volume in the 3D space of the point cloud that includes a set of points that has a high probability of representing a certain object. To that end, the deep neural network system may determine 3D bounding boxes of a predetermined size and location in the 3D space of the point cloud which have a high likelihood of containing points representing an object. The deep neural network system of the object detector may be configured to receive the point cloud (or a subset (e.g. a patch) of the point cloud) and a 3D grid 207 at its input. As depicted in FIG. 2B the 3D grid may define nodes 207 of a certain density in the 3D space of the point cloud. The nodes of the 3D grid may define centers for object proposals in the 3D space. This way, the deep neural network system of the object detector may define an object proposal network configured to determine object proposals, e.g. 3D bounding boxes, located on the nodes of the 3D grid, wherein the 3D grid comprises a plurality of nodes which spans the 3D space of the point cloud. Each of the 3D bounding boxes (which may be referred to as anchors) is associated with features which are determined on the basis of the feature vectors computed by the feature extractor. Hence, given a point cloud as depicted in FIG. 2A and a 3D grid of nodes as depicted in FIG. 28, the deep neural network system of the object detector may determine 3D bounding boxes, each having a center located on one of the nodes of the 3D grid and each containing features that are relevant for points in the 3D bounding box. This is schematically shown in FIG. 2C. As shown in this figure, the object detector generates anchors associated with different objects, e.g. anchors associated with a first object $208_{1-3}$ and anchors associated with a second object $206_{1-2}$.

The object detector may comprise a further deep neural network which is configured to classify features that are located in each of the anchors. This network may define an object classification network that is trained to receive features associated with points located in an anchor as its input and to use these features for determining whether the anchor contains points that represent a predetermined object.

A mask generator 108 may process points within an anchor that has been classified by the object classification network to contain a predetermined object. The center and the dimensions of an anchor as inputted in the object proposal network is determined by the 3D grid. Thus, an anchor does not necessarily provide an accurate position of the center of an object and its dimensions. In order to generate an accurate position of the object, the mask generator may include a deep neural network that is trained to determine the center and the dimensions of a 3D bounding box that contains points representing a predetermined object. This neural network may be referred to as an objection location predictor network.

Furthermore, based on an accurately positioned and dimensioned 3D bounding box, the mask generator may select points that are located in the 3D bounding box.

The points in the 3D bounding box may include points representing the object and point that are part of a background. The classification of the points may be performed using a deep neural network, which may be referred to as mask predictor network. The mask predictor network may e.g. classify points as belonging to a predetermined object, e.g. one or more different objects. In some embodiments, it may classy the points which belong to an unknown object inside the 3D bounding boxes as background. Positively classified points inside each bounding box by the mask generator network may be referred to as a 'mask'. The object classification network, the object location predictor network and the mask predictor networks are described hereunder in more detail.

FIG. 2D depicts the results of this process, including three segmented sets of points $212_{1-3}$, wherein each set of points represents an instance of a first object (e.g. a spherical object), and two segmented sets of points, wherein each set of points $214_{1-3}$ represents an instance of a second object (e.g. a cylindrical object).

The deep learning system as described with reference to FIG. 1 and FIG. 2 is capable of accurate and efficient object detection and instance segmentation of 3D point clouds by using deep neural networks that are capable of directly processing points of the point cloud so that voxelization of a point cloud as known from prior art solution is not required. The deep neural networks may be based on deep multi-layer perceptron (MLP) networks.

Figure 3:
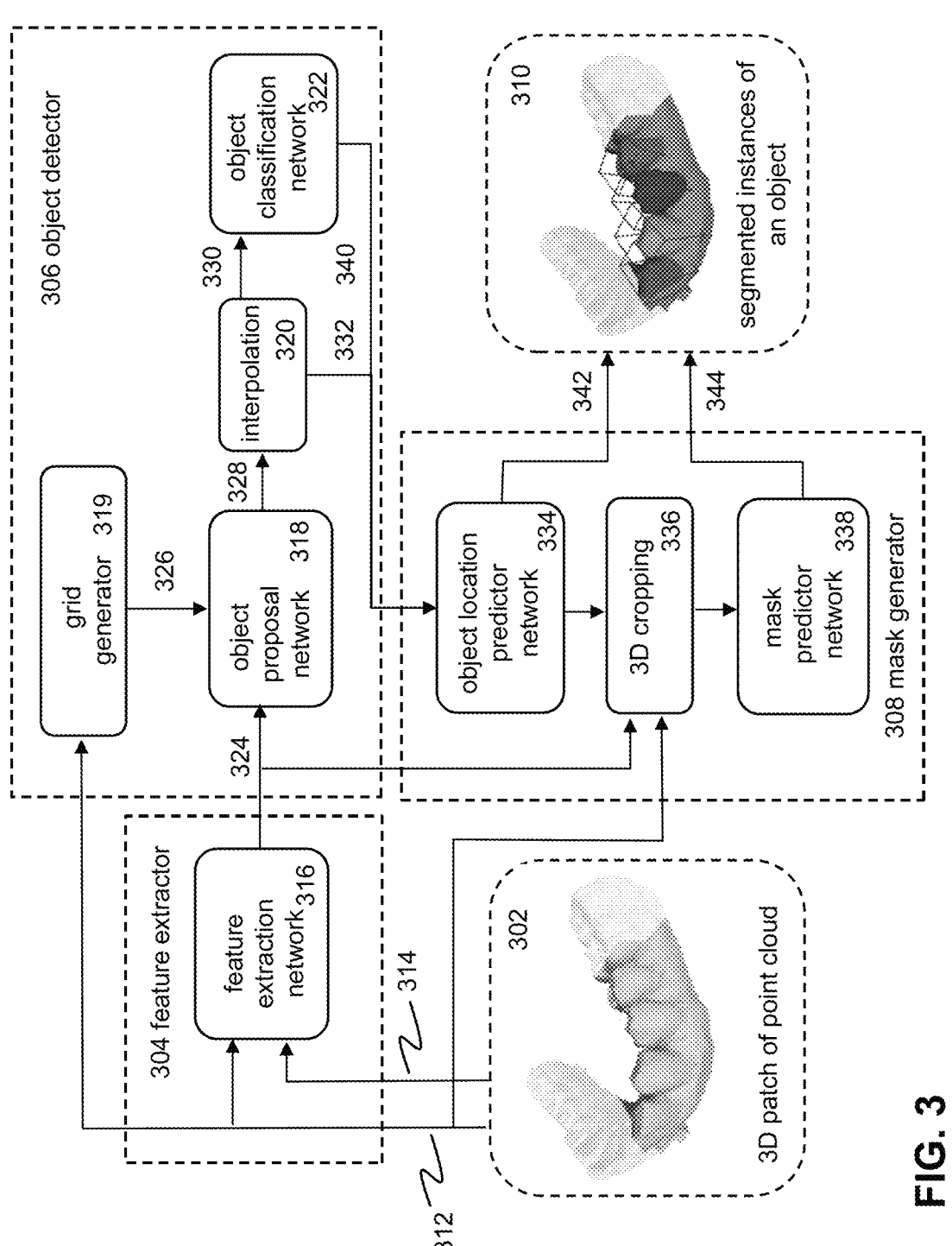
FIG. 3 depicts a deep learning system for object detection and instance segmentation of 3D point clouds according to another embodiment of the invention.

FIG. 3 depicts a schematic of a deep learning system for object detection and instance segmentation of 3D point clouds according to an embodiment of the invention. The deep learning system in FIG. 3 is configured to apply instance segmentation on a point cloud that is generated by a 3D optical scanner. Here, instance segmentation refers to the process of assigning a unique label to all points belonging to an instance of an object, e.g. a tooth, using a computational model. Typically, the computational model includes one or more trained neural networks.

In an embodiment, the 3D optical scanner may be an intra-oral scanner (IOS) for scanning teeth. A point cloud generated by an IOS may be referred to as an IOS point cloud. Automatic instance segmentation of an IOS point cloud in sets of points that represent individual teeth is highly desirable for many applications in dentistry, implantology and orthodontics. IOS point clouds may include a large set of points, typically hundreds of thousands of points of more, comprising high-resolution information about the anatomic structure of the crowns and the gums (the gingiva). In some embodiments, the point cloud can also be transformed in to a mesh data structure (after e.g. applying a triangulation algorithm on the points).

As shown in FIG. 3, input data 302 such as an IOS point cloud or a patch of an IOS point cloud, may be provided to a feature extractor 304. A patch of an IOS point cloud may include n points, where wherein n may vary between different patches. The input data may include coordinates 312 defining points of the point cloud, wherein the coordinates may be defined based on a Cartesian coordinate system x,y,z. Additionally, in embodiments in which the points define a 3D surface mesh, the input data may also include normal vectors 314 of surfaces defined by a number of points. A mesh may define a graph including a number of vertices at locations defined by the points in the point cloud. Adjacent vertices may be connected by edges to each other as a result of triangulation algorithm. Each triangle includes three adjacent vertices in mesh which may define a surface (sometimes referred to as a 'face'). This way, it is possible to compute a normal vector which is oriented perpendicular to such a face. In order to assign the normal vector to the vertices (points), an average of all normal vectors of faces (i.e. triangles) to which each vertex contributes may be calculated. Hence, in case of a patch of n points of a 3D surface mesh, the input data for the feature extraction network may be represented as an n×6 matrix, including n point coordinates and n associated normal vectors. More generated input data may include 3D position of a point and one or more further attributes (normal vector, color, etc.).

The feature extractor may comprise a feature extraction network 316 (which may also be referred to as a backbone network). The feature extraction network is a deep neural network that may be trained to receive a point cloud or a patch of a point cloud at its input and determine feature vectors 324 for points of the point cloud. In an embodiment, the feature extraction network may be trained to determine a feature vector for each point of the point cloud. A feature vector may define a plurality of features describing geometrical information around each point of the point cloud. For example, in an exemplary implementation the feature extraction network may generate n feature vectors (where n denotes the number of input points), wherein each feature vector may comprise a plurality of feature elements, e.g. 256 elements.

Figures 5, 6:
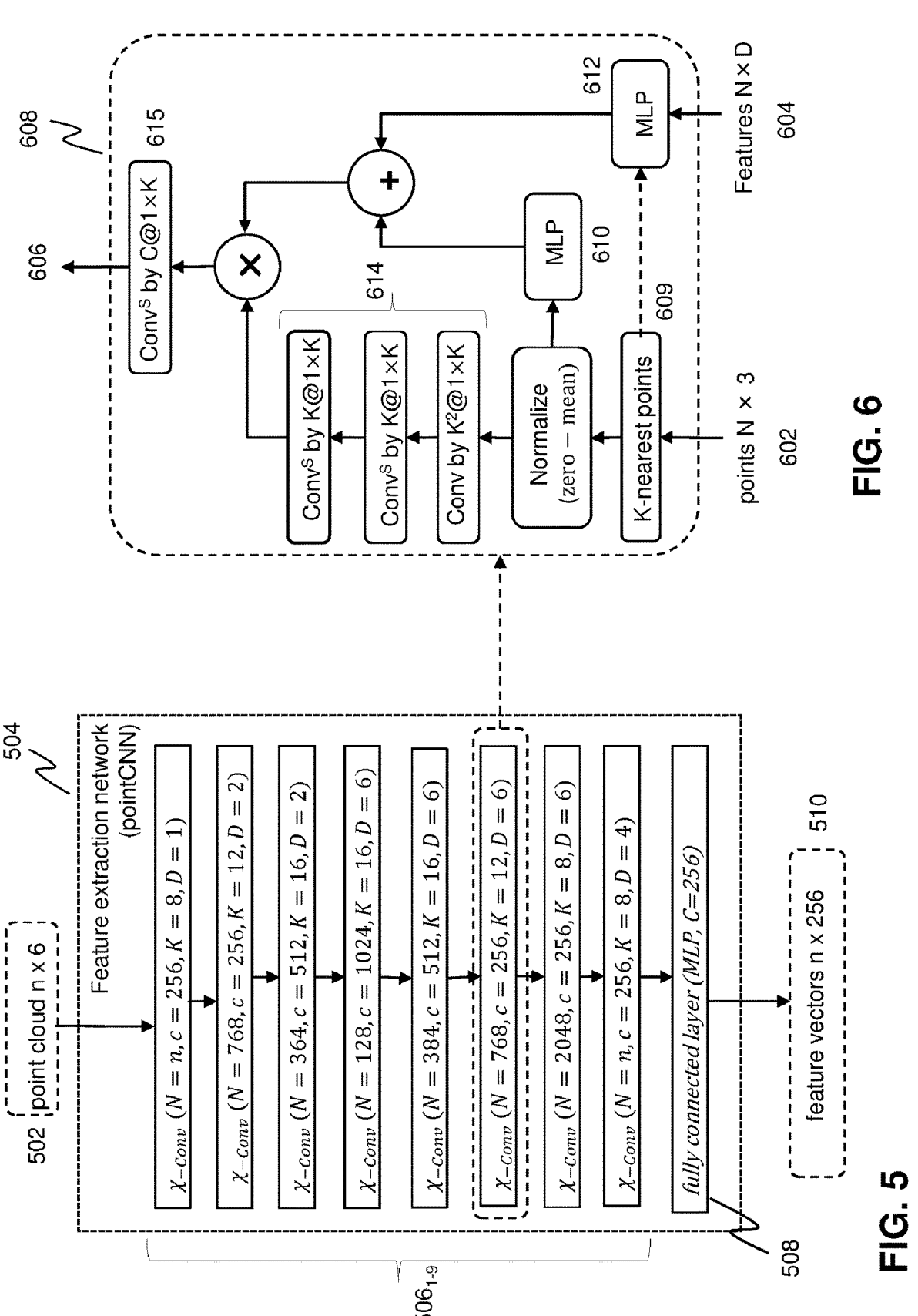
FIG. 5 depicts a schematic of part of a feature extraction network according to an embodiment of the invention.
FIG. 6 depicts a schematic of part of a feature extraction network according to another embodiment of the invention.

In an embodiment, the feature extraction network may be implemented as a deep multi-layer perceptron (MLP) based network, which is applied to the entire point cloud (or—depending on hardware limitations—a patch of a point cloud). In an embodiment, the MLP-based network may be configured as a so-called PointCNN network. The PointCNN network is described in the article by Li et al. "PointCNN: convolution on $\chi$-transformed points", arXiv: 1801.07791v5 of 5 Nov. 2018, to be published in Neural Information Processing Systems (NIPS) 2018. Although many choices for the feature extractor network (backbone network) can be made, the advantage of the PointCNN network architecture, which is described in more detail with reference to FIGS. 5 and 6, is that it allows processing of fine details of a point cloud and that it has a small model size. The output of the the feature extraction network may be an n×256 matrix of features (where n denotes the number of input points). A feature vector associated with a point of the point cloud may contain rich geometrical information in a volume around that point. In other embodiments, other deep neural networks that are capable of extracting features from a point cloud data set may be used for the feature extraction network, including but not limited to PointNet (Qi, C. R., et al.: *Pointnet: Deep learning on point sets for 3d classification and segmentation*. Proc. Computer Vision and Pattern Recognition (CVPR), IEEE 1(2), 4 (2017)), Qi, Charles Ruizhongtai, et al.; PointNet++: *Deep hierarchical feature learning on point sets in a metric space*; Advances in Neural Information Processing Systems. 2017, PointGrid (Le, T., et al.: Pointgrid: *A deep network for 3d shape understanding*. In: Proceedings of the IEEE Conference on Computer Vision and Pattern Recognition. pp. 9204-9214 (2018)), MCCNet (Hermosilla, P., et. al: *Monte carlo convolution for learning on non-uniformly sampled point clouds*. In: SIGGRAPH Asia 2018 Technical Papers. p. 235. ACM (2018)), PointCNN (Li, Y., et al: *Pointcnn*, arXiv preprint arXiv: 1801.07791 (2018)), SpiderCNN (Xu, Y et al, *SpiderCNN: Deep learning on point sets with parameterized convolutional filters*, ECCV 2018.

The feature vectors determined by the feature extraction network may be provided to the input of the object detector 306 which includes a so-called object proposal network 318. The object proposal network may be trained to receive feature vectors 324 from the feature extraction network and a 3D grid of nodes, which define so-called anchors in the 3D space of the point cloud (or a patch thereof). The 3D grid defines a 3D arrangement of nodes that spans the 3D space of the point cloud. An anchor may define a a 3D bounding box having a central position $[x_a,y_a,z_a]$ and dimensions [w,d,h]. The center of an anchor may be determined by a node of the 3D grid.

Points of a point cloud typically define 'surface points', i.e. samples of surfaces of objects as determined by a 3D optical scanner. An example of such scanner is an IOS scanner. Features computed by the feature extraction network typically comprise local geometrical information on a manifold of the 3D space. In other words, such rich geometrical information may encode the local surface of objects as local curvature of a surface in the 3D space. However, for a regression task such as accurate localization of a 3D bounding box encompassing an object, the model requires to aggregate the 3D geometrical information from the 3D surface mesh into the void space of the 3D space of the point cloud, such as the void space inside objects. For example, for accurate object determination the model requires 3D spatial information on different parts (e.g. sides) of a collection of points of the point cloud that represent an object. Voxelization of the point cloud and applying a 3D CNN to process the voxelized volumetric data would be a conventional approach to solve this problem. However, as described before, voxelization of a non-uniform point cloud will seriously limit the performance of the neural network as to the quantization error due to converting the point cloud into volumetric data degrades the fine-details of the geometric information.

In order to solve the shortcomings in the prior art, the object proposal network may be configured to distribute and transfer geometrical rich information from the surface of objects (as encoded in the feature vectors which are determined by the feature extraction network) into the entire 3D space (e.g. into void space inside of an object such as a tooth). In an embodiment, a so-called Monte Carlo Convolutional Network (MCCNet) architecture may be used for implementing the object proposal network 318. The MCCNet architecture, which is described in more detail with reference to FIGS. 7 and 8, may include one or more multi-layer perception (MLP) based networks. In particular, the MCCNet may comprise several modular MLP sub-networks including at least two hidden layers which have a function that resembles a set of convolution kernels. These layers may be referred to as a convolutional layer of the MCCNet. This way, the MCCNet is capable of computing a convolution on an arbitrary (new) point-set within the kernel's field of view (FOV), regardless of its presence within the set of input points. In other words, a new points set of locations is generated by the outputs of the convolution layers. Those locations can be any arbitrary location on the point cloud, even in the locations where there is no sample in the point cloud. This way, the MCCNet allows the computation of the convolution of a non-uniform distribution of points.

The MCCNet is configured to transfer features computed by the feature extraction network from the point cloud domain (features associated with a point in the 3D space of the point cloud) to a new domain that is based on a 3D grid of nodes, which spans the 3D space of the point cloud. This new domain may be referred to as the grid domain, wherein features are associated with the nodes of a 3D grid that spans the 3D space of the point cloud (the input space). In an embodiment, the 3D grid of nodes may be provided as input data to the network. In an embodiment, a grid generator 319 may generate a 3D grid 326 of a certain node density and provide the 3D grid to the input of the object proposal network. The grid generator may be configured to generate a 3D grid based on information of the points of the point cloud. For example, the grid generator may determine the density of the nodes of the 3D grid based on the point cloud that is provided to the input of the system of FIG. 3. Determining the nodes of the 3D grid on the basis of the point cloud ensures that sufficient details of the feature vectors associated with points of the point cloud are transferred by the MCCNet to the 3D grid domain.

Thus, as shown in FIG. 3, the object proposal network may receive feature vectors from the feature extraction network and a 3D grid 326 which spans the entire 3D space of the point cloud or at least a substantial part thereof. Based on this input, the object proposal network may be configured to determine 3D anchors, which may be used as object proposals, i.e. a volume of a certain shape, e.g. 3D bounding boxes, comprising points that represent an object. The 3D bounding boxes may have any suitable shape. e.g. rectangular, spherical, cylindrical, etc.

The object proposal network does not make any assumptions regarding the possible positions of objects in the 3D space. In an embodiment, the 3D grid may be a uniform grid defining nodes that are uniformly distributed in the 3D space of the point cloud. In that case, the spatial resolution of the 3D grid may determine the performance of the model in terms of accuracy and computing power. Choosing a low-resolution 3D grid may lead to positioning too few anchors inside small objects (e.g. incisor teeth in case of IOS data), whereas a high-resolution grid may cause the computation to be inefficient.

In order to improve the accuracy and the efficiency of the model, in an embodiment, instead a uniform grid, a non-uniform grid may be provided to the network. The non-uniform 3D grid may include a dense distribution of nodes close to the surface(s) of an object and a sparse distribution of nodes at distances further away from the surface(s) of an object. A non-uniform 3D grid may be determined by the grid generator based on the point cloud that is fed to the input of the network and an initially dense uniform 3D grid. The non-uniform 3D grid may be obtained by filtering out nodes of the initial dense 3D grid using the distance between a node and point in the point cloud that is closest to that node. Furthermore, a predefined lower bound for the grid resolution may be used. Nodes from the 3D grid which have a nearest neighbour point from the point cloud farther than a threshold, are removed if there are any points in the grid that is closer to them, compared with the threshold.

The above-mentioned properties of the object proposal network enable transfer of features from the point cloud domain (features associated with the position of a point in the 3D space of the cloud) into the above-described grid domain (features associated with the position of a node of the 3D grid that spans the 3D space of the point cloud). In an embodiment, the object proposal network may generate m 3D anchors (e.g. m 3D bounding boxes associated with m nodes of the 3D grid), each having a center that coincides with a node of the 3D grid that was fed to the input of the object proposal network. Furthermore, for each node of the 3D grid the object proposal network may determine geometrical information (features) that belong to a 3D anchor that has this node as its center coordinate. An object classification network 322 may determine whether an anchor includes points representing an object or not on the basis of the features in the anchor. Evaluation of the features in the anchors by the object classification network may result in classified 3D anchors, e.g. 3D bounding boxes, wherein each classified 3D anchor contains points that belong to a certain object. The anchors that are classified and not containing an object are discarded.

A first MLP network from the input of the MCCNet may function as a convolutional layer for transferring the features of the point cloud domain to the grid domain. The data is further processed by the hidden layers of the MCCNet. Based on the FOV of each convolutional kernel, the geometrical information of 'surface points' will be distributed over the nodes of the 3D grid. In an embodiment, each node of the 3D grid may represent a position (e.g. a center) of one anchor (k=1). In another embodiment, each node of the 3D grid may represent a position of multiple anchors (k>1), wherein k anchors associated with a node may have different aspect ratios. Hence, the total amount of 3D anchors generated by the object proposal network 318 may be k×m.

Based on the features inside each 3D anchor, the object classification network 322 may predict whether the 3D anchor contains an object or not. To that end, the object classification network may determine a score for each 3D anchor, wherein the score may represent a probability that a 3D anchor includes an object instance or not. A threshold may be used to determine if the score indicates that a 3D anchor contains points defining an object.

Object classification network 322 may be implemented as a fully-connected MLP with fixed-length input. In that case, the feature set inside each anchor needs to be of a fixed length. Therefore, an interpolation module 320 between the object proposal network 318 and the object classification network 322 may be used to determine a fixed set of features for each 3D anchor. For example, in an embodiment, the interpolation module may determine (interpolate) each 3D anchor to have s×s×s nodes. Values of s might? be between 2 and 12. This way, each 3D anchor may have a feature set of fixed length. For example, an interpolation using nearest neighbor nodes (e.g. the three nearest neighbors) of the grid and the weighting of their feature vectors based on their distance to a new node in 3D space may be used. Thus, the interpolation module may determine for the k×m 3D anchors as determined by the object proposal network an output matrix of k×m×s³ features.

If the object detector has determined that a point cloud comprises one or more 3D anchors comprising an object, the mask generator 308 may be triggered to classify points in each of the one or more 3D anchors. The classification process may determine which points in an 3D anchor may represent an object. In that case, an objection location predictor network may receive information 340 about which 3D anchors are classified by the object classification network as containing an object. A classified 3D anchor 332 may be provided to an object location predictor network 334, which is configured to determine a volume that accurately encompasses the object. This volume may be referred to as an object volume. The object volume may have a center position that accurately matches a center position of the object. Furthermore, the dimensions of the object volume may accurately match the outer dimensions of the object. In an embodiment, the object location predictor network may generate information to reposition and rescale a classified 3D anchor into an object volume.

The position and dimension of the object volumes may be provided to a 3D cropping module 336, which may use the position and the dimensions to crop object patches out of the point cloud. Each object patch may comprise points of the point cloud that are positioned within an object volume. This way, each object patch may define a set of points that comprise points representing an object as predicted (detected) by the object detector 306. In an embodiment, the 3D cropping module may use each of the m×k object volumes to crop p points from the point cloud. Furthermore, each of the p points may be associated with one of the n feature vectors generated by the feature extraction network.

Thus, for each object volume, the 3D cropping module may extract p points from the point cloud, wherein each point is associated with a feature vector 324, leading to m×k×p feature vectors, wherein each feature vector may have a plurality, e.g. 256, of feature elements.

Object patches and associated feature vectors may be provided to a mask predictor network 338, which is configured to classify points in an object patch into classified points, i.e. points that belong to an object and points that do not belong to an object (e.g. the background). This classification process may result in segmented instances of points that represent an object, e.g. segmented tooth instances in an iOS patch 310 as depicted in FIG. 3.

Thus, from the above it follows that three individual MLP-based networks may be employed to process the output of the object proposal network. The first network (the object classification network) is responsible for predicting whether each point in the grid domain is positive or negative. A node on the grid is considered positive if it belongs to at least one positive anchor. Positive anchors are those anchors which have a high IoU (overlap) with an object in data. Thus, the first network is employed for classification of the grid nodes. All points inside the positive anchors are processed by two other networks, the object location predictor network and the mask predictor network. One of these networks is trained to estimate the spatial displacement between center of a positive anchor (candidate) with its assigned ground truth center. The second network (the object location predictor network) is responsible for predicting the difference values between the size of a positive anchor (e.g. width, height, and depth of a 3D cube) with its equivalent values of the ground truth. In total, one of the networks performs a classification on grid nodes and the next two networks have been employed for solving a regression problem. In order to segment all points belonging to an object that encompass by a 3D box, a subnetwork is employed. This network, which is called a mask predictor network, is responsible for classification of the points inside each 3D bounding boxes.

FIGS. 4A and 4B depict flow-diagrams of processes for detecting and instance segmentation of points clouds according to various embodiments of the invention. These processes may be executed by modules of the deep learning system as described with reference to FIG. 1-3 above. FIG. 4A depicts a flow-diagram of a process for detecting objects in a point cloud by a system of trained neural networks. As shown in the figure, the process may include a first step 402 of receiving a point cloud, the point cloud including points representing one or more objects in a 3D space of the point cloud. In a next step (step 404), first point cloud features of the point cloud may be determined. In an embodiment, the first point cloud features may be determined by a first type of deep neural network based on the points of the point cloud. The first point cloud features may define local geometrical information about the point cloud at the position of each point of the point cloud. In an embodiment, the first point cloud features may define first feature vectors. Each feature vector associated with a point may define geometrical information about the space around that point, e.g. geometrical information about the presence or absence of points within a certain volume around that point, relative distances between those points and local curvatures defines by these points.

A third step 406 may include transforming, by an object proposal network, the first point cloud features into second point cloud features. Here, the second point cloud features may define local geometrical information about the point cloud at the position of nodes of a 3D grid spanning the 3D space of the point cloud. A further fourth step (step 408) may include generating one or more object proposals based on the second features. An object proposal may define one (or more) 3D bounding box positioned around a node of the 3D grid, wherein the 3D bounding box may contain points of the point cloud that may define an object. Such 3D bounding box generated by the object proposal network may also be referred to a 3D anchor.

Each of the 3D anchors may be positioned around a node of the 3D grid and a second feature vector associated with each of the 3D anchors may define geometrical information within the space defined by the 3D anchor. The determination of the second feature vectors may include providing the first feature vectors and the nodes of the 3D grid to the input of the second deep neural network and the second deep neural network providing the second feature vectors for each of the 3D anchors at its output.

A fifth step 410 may include selecting the feature set from the second features that are located in the 3D anchor; and determining, by an object classification network, a score for the 3D anchor on the basis of this feature set. The score may indicate a probability that the 3D anchor includes points defining an object or part of an object.

The process depicted in FIG. 4A provides an accurate and efficient way to predict objects in a point cloud. The determination of the first feature vectors may include providing the points of a point cloud to the input of the first deep neural network and the first deep neural network providing first feature vectors for the points of the point cloud at its output. The process is directly applied to the point cloud (the input data) without the need for voxelization or the like so that all geometrical information embedded in the point cloud can be used for object detection. Furthermore, the process determines objects in a point cloud by evaluation of features in a new domain, the grid domain, without the need to classify each point in the point cloud. This way, the process provides a very efficient way of detecting (predicting) if points representing a predetermined object are present in a point cloud.

FIG. 4B depicts a flow-diagram of a process for instance segmentation of a point cloud. This process may be executed after the object detection process as described with reference to FIG. 4A. The instance segmentation process may start with a step 412 of receiving a feature set contained in a 3D anchor that is positively classified by an object classification network for containing an object instance. A further step (step 414) may include determining an object volume, by an object location predictor network. The object location predictor network may generate center location of an object instance. Alternatively, the object location predictor network may generate outer dimensions of an object instance. In an embodiment, the center position of the object volume may coincide with the center location of the object instance. In another embodiment, the dimensions of the object volume may match the outer dimensions of the object instance.

The position and dimensions of the object volume may be used to crop a set of points from the point cloud and to crop a set of point cloud features from the first point cloud features (step 416). Classified points may be determined (step 418), by a mask prediction network. The classified points may be determined based on the set of first point cloud features, wherein the classified points may include first classified points belonging to the object instance and second classified points not belonging to the object instance. The cropped set of points and matching point features can be inputted in a mask prediction network (step 418), that classifies each point as being part of either the object instance or not (background).

Hence, the process steps depicted in FIG. 48 allows efficient instance segmentation of points of a point cloud by accurately determining the volume in the 3D space of the point cloud that contains the points representing the object. This way, the process allows segmentation of the points without the need to classify each point of the point cloud as known from conventional semantic segmentation processes.

FIGS. 5 and 6 depict a schematic of part of a feature extraction network according to an embodiment of the invention. In particular, these figures depict a schematic of a deep neural network architecture of a feature extraction network 504 that is capable of directly processing points of a point cloud 502, which may be represented by n points, wherein each point may be represented by cartesian coordinates and, optionally, a normal vector. The deep learning network may be configured as an MLP-based network. In an embodiment, the MLP-based network may have a PointCNN network architecture (as already shortly mentioned in the description of FIG. 3). As shown in FIG. 5, the MLP-based network model 502 may include a stack of so-called $\chi$-Conv layers $506_{1-9}$. Each $\chi$-Conv layer may be configured to weight and permute the input points and their corresponding features, prior to processing by a convolution operator.

The structure of a $\chi$-Conv layer is depicted in more detail in FIG. 6. A $\chi$-Conv layer is characterized by the parameters N, c, K and D. Each $\chi$-Conv layer returns N representative points with c channels, wherein the representative points are the points (representing a position in the 3D point cloud space, i.e. the input space) at which a convolution is computed. Furthermore, the channel represents the dimension of the feature vector. For example, a point associated with 256-dimensional feature vector has 256 channels. The constant K is the neighboring point number for each representative point, and D is the dilation rate of a $\chi$-Conv layer, i.e. the ratio between the points that are input to the layer and the points that are generated as output.

The field of view (FOV) of each X-Conv layer may include a fixed set of K-nearest neighbor (KNN) points 609, i.e. the points nearest to the location of the point at which the convolution is computed. Additionally, the $\chi$-Conv layer may include two or more MLP networks 610, 612. These MLP networks learn a $\chi$-transformation of K×K for the coordinates of K input points. The outcome of the $\chi$-Conv layer is the aggregation and projection of KNN point features into a representative set of points, after which a convolution is applied to.

The PointCNN model depicted in FIGS. 5 and 6 is capable of learning local geometrical correlations between points in the point cloud. It has a considerably lower amount of learning parameters in comparison with other known deep learning models for point clouds. This is beneficial, because it is less prone to severe overfitting on a small dataset. The inputs to the network may be points of the point cloud 506, (e.g. n points wherein each point as x,y,z coordinates and (optionally) elements of a normal vector thus defining an n×6 matrix). The output of the network 510 may be a set of feature vectors (e.g. n vectors wherein each vector has a plurality of feature elements, e.g. 256 feature elements), wherein each feature vector is associated with a point of the point cloud. A feature vector may be a multi-element vector (in the example 256 elements), wherein each element of the vector represents a class probability.

FIG. 7 depicts a schematic of object proposal network according to an embodiment of the invention. As shown in the figure, the architecture of the object proposal network 704 comprises a multi-layer stack of MLP layers. The network may be referred to as a Monte Carlo Convolutional Network (MCCNet), which includes Monte Carlo (MC) spatial convolutional layers $712_{1-4}$, batch normalization (BN) layers $714_{1-6}$ and 1×1 convolution layers $716_{1-3}$. The object proposal network may be configured to receive feature vectors defined in the point cloud domain 702 (i.e. feature vectors associated with a point cloud wherein each feature vector defines geometrical information in the neighbourhood of a point of the point cloud) and a 3D grid of nodes 707. In an embodiment, the 3D grid of nodes may be generated by a 3D grid generator 708. In some embodiments, a non-uniform 3D grid may be used as the 3D grid. In that case, the 3D grid generator may be determined by filtering nodes from a dense uniform 3D grid 710. The 1×1 convolution layers have $C_{in}$ input channels and $C_{out}$ output channels. These layers may be used reducing or increasing the number of point features.

As shown in the figure, the first MC spatial convolution layer 712₁ may be configured to receive feature vectors of the point cloud domain and m nodes of a 3D grid. Based on this input, the convolutional layer transforms the feature vectors of the point cloud domain to feature vectors of the grid domain. The input data will be further processed by the hidden layers of the network. Based on the FOV of each convolutional kernel, the geometrical information of 'surface points' will be distributed over the nodes of the 3D grid, leading to m feature vectors in the grid domain 706.

The Monte Carlo convolution layer is a convolutional layer that is capable of calculating a convolution for unstructured data such as points of a point cloud. The MC convolutional layer is described in the article by Hermosilla et al, *"Monte Carlo convolution for learning on non-uniformly sampled point clouds"*, ACM Transactions on Graphics, Vol 37, No, 6, article 235, November 2018. As shown in the figure, a MC convolutional layer may be characterized by four parameters, wherein the notation A|B|C|D indicates that the layer is configured to map points from level B to level C using a field of view (FOV) equal to D. The constant A determines the dimension of the feature vectors at the output side of the layer, FIG. 8 schematically illustrates the working of a Monte Carlo convolutional layer which is configured to transform features (from the point cloud domain to the grid domain. A convolution operation may be defined as an integral of a product of two functions $f$ and g:

$$(f*g))(x)=\int f(y)g(x-y)dy$$

Where function $f$ is a scalar function on $R^3$ to be convolved (in this case the feature vectors determined by the feature extraction network) and function g is the convolution kernel, which is a scalar function on $R^3$. In particular, function $f$ may define a feature function for a set S of discrete samples $x_i \in S$ (given data points). If no other information is provided besides the spatial coordinates of each point, $f$ may represent a binary function which has a value "1" at the samples surface and a value "0" otherwise if a point is only represented by its spatial coordinates. In other variants, function $f$ may take also other type of input information into account including e.g. colour, normals, etc.

For a hierarchical network structure (e.g. a multi-layer network), the output from a first convolution layer represents features that form the input to the subsequent convolution layer. As the value of g only depends on relative positions, the convolution integral is translation invariant. Evaluating a convolution integral over the entire point cloud may be problematic for a large dataset, hence the domain of g may be limited to a sphere centered at 0 and radius 1. To support multiple radii, the input of g may be normalized by dividing it by the receptive field r, i.e. the radius of the spherical field of view (FOV) of the convolution kernel. In particular, r may be chosen to be a fraction of the scene bounding box diameter b, e.g. r=0.1·b. Since the point cloud data is normalized to have variance equal to one, the diameter of the scene boundary is considered to be equal to one (b=1). This will result in scale invariance. Such relative kernel size will make the processing valid for input scans with different size (diameter). This construction may result in compactly supported kernels that are fast to evaluate.

A multi-laver perceptron (MLP) network may be used for the kernel p, similar to the work of Hermosilla et al as cited above. In an embodiment, the MLP network may determine a spatial offset δ=(x−y)/r, comprising of three normalized coordinates and dividing them by the receptive field r. The output of MLP network is a single scalar. To balance accuracy and performance, a number of hidden layers, e.g. two or three, may be used wherein each hidden layer may include a plurality of neurons. In an embodiment, a hidden layer may include 6-12 neurons, preferably 8 neurons. The number of parameters in the MLP kernel increases with the dimension of input and output vectors. Hence, in an embodiment, one MLP with multiple outputs (which represents different g kernels) may be used to reduce the number of trainable parameters (e.g. by a factor of 8 if the output of MLP produces 8 different g's). As the output of the MLP network is differentiable with respect to its input, a backpropagation algorithm may be used to update the parameters of the kernel. In an embodiment, a gradient-decedent optimization scheme may be used to train the network.

To compute the convolution in each sampled point, the convolutional integral needs to be evaluated. Since only a set of samples of the feature function $f$ is available, a so-called Monte Carlo integration may be used to determine an estimate of the convolution at a point x in the 3D point cloud space. In the Monte Carlo integration approach, a set of random samples may be used to compute the value of the integral. Based on this approach, an estimate of the convolution for a point x may be given by the following expression:

$$(f*g)(x) \approx \frac{1}{|N(x)|}\sum_{j\in N(x)} \frac{f(y_j)g\left(\frac{x-y_j}{r}\right)}{p(y_j\,|\,x)}$$

where N(x) is the set of neighbourhood indices, i.e. a set of indices belonging to the neighbouring points in a sphere of radius r (the receptive field), and pix is the value of a probability density function (PDF) at point $y_i$ when point x is fixed (i.e. the convolution is computed at point x). Here, x is an arbitrary output point in the 3D space of the point cloud that does not necessarily needs to coincide with a point of the set of input points $y_i$. In an embodiment, the output of the first convolution layer of the MCCNet may be points of a 3D grid (in the application the points of the 3D grid are also referred to as nodes to distinguish them from the points of the point cloud) In deeper layers (2ⁿᵈ and subsequent layers), the output points of each layer may be a subset of points of the initial 3D grid. These output points are referred to as representative points. This property of the Monte Carlo convolution allows re-sampling to other levels or other regular domains (e.g. a uniform 3D grid of nodes) or irregular domain (a non-uniform 3D grid of nodes).

In case the nodes of the 3D grid are distributed nonuniformly, for each point $y_i$, the value of pix will be different and may not only depend on the sample position $y_i$ but also on the radius r of the receptive field, i.e. the FOV, and the distribution of the other points in the receptive field. As the sample density is unknown for a given point cloud, it may be approximated by a technique which is referred to as kernel density estimation. The estimated function has a high value where samples are dense and a low value where samples are sparse. This function may be computed based on the following expression:

$$p(y_j \mid x) \approx \frac{1}{|N(x)|\delta^3} \sum_{k \in N(x)} \left\{ \prod_{d=1}^{3} h\left(\frac{y_{j,d} - y_{k,d}}{\sigma}\right) \right\}$$

where $\delta$ is the bandwidth which determines the smoothing of the resulting sample density function, h is the Density Estimation Kernel, a non-negative function whose integral equals 1 (e.g. a Gaussian function), d is one of the three dimensions of $R^3$ and $\sigma$ being a radius of a Gaussian window. Instead of Gaussian kernel density estimator other types of functions may be used including but not limited to an Epanechnikov, a Quartic, or a tri-cube kernel estimator.

The application of the MC convolution on point cloud samples at node position x 800 in the 3D grid 808 is illustrated in FIGS. 8A and 8B. FIG. 8A depicts the 3D grid of nodes in the 3D inputs space of the point cloud (the input space). For clarity reasons, the points of the point clouds are not shown.

FIG. 8B depicts a more detailed illustration of an area around node X. The figure depicts node x and points $y_i$ of the point cloud around node x. For clarity, in FIG. 8B the nodes of the 3D grid 808 other than node x are not shown. To compute the convolution, the features $f(y_i)$ associated with points $y_i$ within a spherical field of view (FOV) 802 (with radius equal to r) are processed by the MLP kernel. For each point $y_i$ 804 of the point cloud in the FOV, a point density function (PDF) may be computed locally having a Gaussian window 806 having a radius equal to $\sigma$. It is noted that instead of a regular 3D grid of nodes an irregular grid of nodes may be used as e.g. described with reference to FIG. 7.

The PDF of a point $y_i$ with respect to a given node x is always relative to all other points in the receptive field. Therefore, the density cannot be pre-computed for a point $y_i$ since its value will be different for each receptive field defined by x and radius r. In case of a uniform sampling (e.g. voxels or a uniform distribution of points such as a uniform grid) the density function p may be set to a constant value for all given $y_i$ points. The output of the convolution as calculated by the MC convolutional layer is differentiable with respect to the input and the learning parameters of the kernel.

Figures 9, 10, 11:
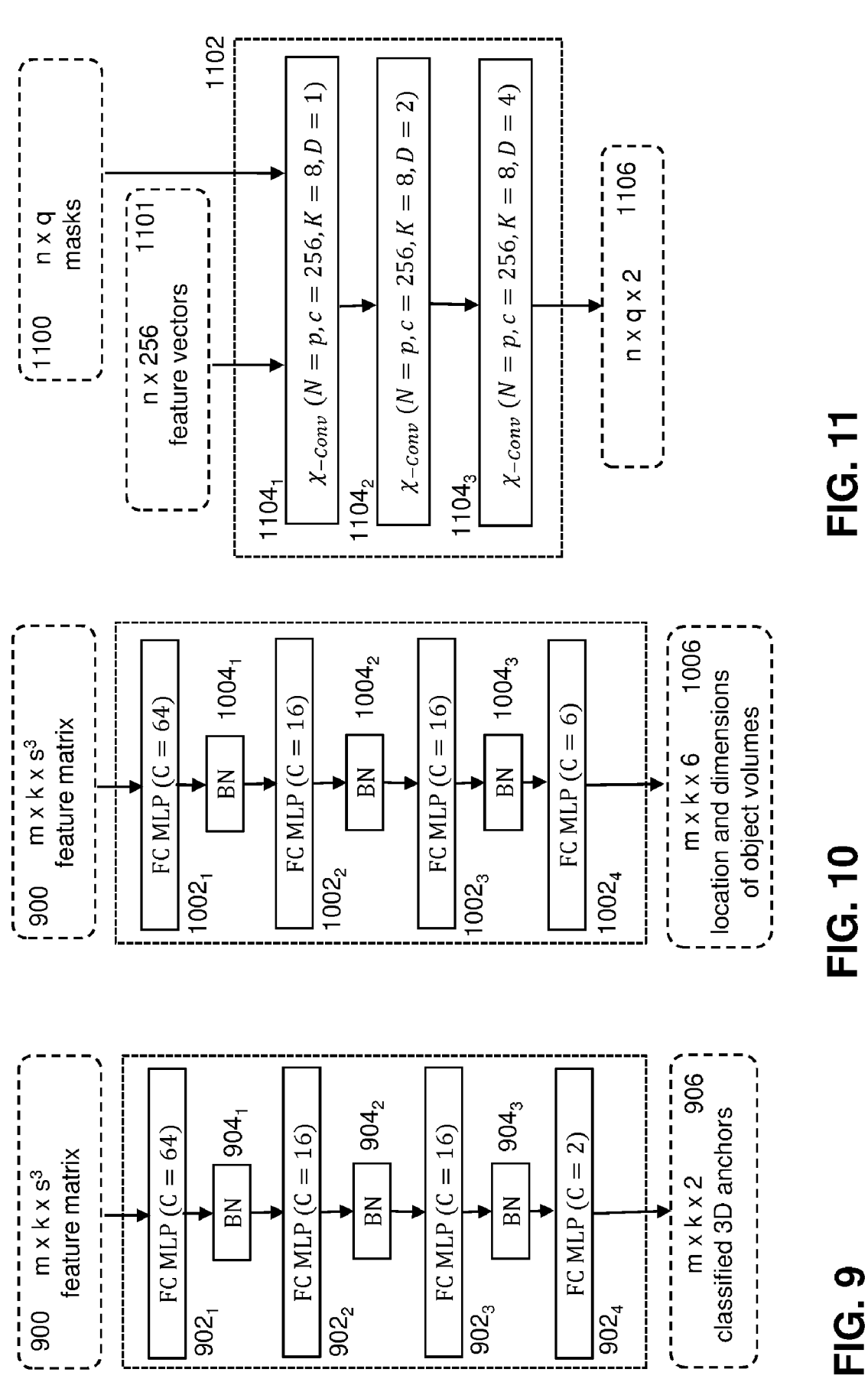
FIG. 9 depicts a schematic of an object classification network according to an embodiment of the invention.
FIG. 10 depicts a schematic of an object location predictor network according to an embodiment of the invention.
FIG. 11 depicts a schematic of a mask predictor network according to an embodiment of the invention.

FIG. 9-11 depict exemplary network architectures for the object classification network, the object location predictor network and the mask predictor network. As shown in FIGS. 9 and 10, the classification and location predictor network are both implemented as a fully-connected (FC) MLP network, which are configured to receive feature vectors from the object proposal network. Each network comprises a stack of FC MLP layers 902$_{1\text{-}4}$, 1002$_{1\text{-}4}$ each being separated by a batch normalization layer 904$_{1\text{-}3}$, 1004$_{1\text{-}3}$. Here, the parameters C indicates the number of neurons in each layer of the fully-connected network.

The object classification network of FIG. 9 may receive feature sets 900 from the object proposal network, wherein each feature set defines features in a 3D anchor. In an embodiment, the feature set may represent a feature matrix. As explained above, each feature set may comprise a fixed number of features. Based on the feature sets, the object classification network may determine classified 3D anchors 906, i.e. 3D bounding boxes, each being centered around a node of the 3D grid. A classified 3D anchor may be associated with a score indicating a probability that a 3D anchor includes an object instance or not. In an embodiment, the object classification network may be trained to perform binary classification. In that case, the network may determine if the 3D anchor comprises points defining an object instance (e.g. a tooth) or not (background). In another embodiment, the object classification network may be trained to determine object instances of different classes, e.g. incisors and molars.

The location predictor network of FIG. 10 may receive feature sets 900 from the object proposal network of positively classified 3D anchors (i.e. 3D anchors comprising an object), and generate an offset defining a central position of the object relative to the node of the 3D anchor and a dimensions offset (e.g. scaling values) defining the dimensions of a 3D bounding box that accurately contains the object relative to the dimensions of the 3D anchor. Thus, the location predictor network may determine a difference (delta) between the 3D anchor dimensions and the dimensions of the object and a difference between the central position of the 3D anchor and the center of the position of the corresponding object. In another embodiment, the location predictor network may determine absolute values of position and dimensions.

FIG. 11 depicts a schematic of a mask predictor network according to an embodiment of the invention. As described with reference to FIG. 3, position and dimensions of each of the object volumes are used by the 3D cropping module to crop object patches out of the point cloud, wherein each object patch may define a set of points that comprise points representing an object as predicted (detected) by the object detector. The 3D cropping module may use each of the m×k object volumes to crop p points from the point cloud, wherein each point is associated with a feature vector, leading to m×k×p feature vectors (each feature vector having a plurality, e.g. 256, of feature elements).

As shown in the figure, each of m×k×q masks which has been constructed by assigning value one to all points inside a detected bounding box and zero to the point outside the box is passed to the mask generator. Furthermore, the first feature vectors for all points with size of n×256 are given to the mask generator. Here, q is the number of detected objects (i.e. tooth). The output of mask generator is binary classification of points inside each bounding box. Thus, each of the m×k×p×3 points 1100 and the m×k×p×256 associated feature vectors 1101 may be provided to the input of the network. The mask predictor network may include an MLP-based network. In an embodiment, the MLP-based network may have a PointCNN network architecture (as e.g. described with reference to FIGS. 5 and 6). Alternatively, the MLP-based network may be based on other neural networks that are capable of processing point cloud including (but not limiting to) PointNet, PointGrid, MCCNet, PointCNN, PointNet++, SpiderCNN, etc. As shown in FIG. 11, the MLP-based network model 1102 may include a (small) stack of χ-Conv layers 1104$_{1\text{-}3}$ wherein each χ-Conv layer may be configured to weight and permute the input points and their corresponding features, prior to be processed by a convolution operator.

The mask predictor network may perform a classification of the points inside each object patch. In an embodiment, it may perform a binary classification classifying the points of an object patch into two classes. For example, in case of IOS data, the binary classification may classify points into first points, e.g. foreground points which may belong to a tooth instance, and second points, e.g. background points which may belong to other teeth or gingiva.

Hence, the deep learning system for object detection and instance segmentation of points clouds as described with reference to FIG. 1-11 above, may provide an accurate and high-performance system for segmenting point clouds without the need for voxelisation. At high level, the deep learning system may be regarded as a 3D point cloud analog of the well-known Mask R-CNN system for instance segmentation of 2D pixel-based images as described in the article by Shaoqing He, K. et al, "*Mask r-cnn*", proceedings of the IEEE international conference on computer vision, pp 2961-2969 (2017). Hence, the deep learning system according to the invention may be referred to as a Mask MCNet, having the feature extraction network as a backbone network, the object proposal network as a region proposal network (RPN) and three predictor networks for classification, regression and mask generation.

Training of the deep learning system as described with reference to FIG. 1-11 may be performed using an end-to-end training scheme e.g. a gradient descent and an Adam learning adaptation technique. For example, 1000 epochs with a batch size of 32 (equally balanced between positive and negative anchors) may be used. The pre-processing of the input may include normalization of the point cloud to obtain zero mean and unit variance.

A training set may include sets of labelled point cloud samples. For example, in case of IOS data, a training set may include optical scans of dentitions, e.g. hundred optical scans or more of dentitions from different adult subjects, each containing one upper and one lower jaw scan (as e.g. depicted in FIG. 3). The IOS data may be recorded using a 3D scanner, e.g. a 3Shape d500 optical scanner (3Shape AS, Copenhagen, Denmark), which comprises 180k points on the average (varying in a range interval of [100k, 310k]). A data set may include scans from healthy dentition with a variety of abnormalities among subjects.

In an embodiment, optical scans may be manually segmented and their respective points may be labeled and categorized according to the FDI standard into one of the 32 classes by a dental professional and reviewed and adjusted by one dental expert (DAM). Segmentation of an optical scan may take 45 minutes on average, showing that segmentation of point clouds is an intensive laborious task for a human.

A loss function may be used to train the networks of the embodiments described in this application. The loss function of Mask-MCNet may include loss contributions from different networks of the Mask-MCNet. In an embodiment, the loss contribution may include a first loss contribution associated with the output of the object classification network, a second loss contribution associated with the object location predictor network and a third loss contribution associated with the mask predictor network. In an embodiment, the loss contributions may be similar to the loss function that was used by Shaoqing He, K. et al, (cited above) for the Mask R-CNN, in which three loss contributions were used, with an equal contribution of each of the three loss contributions.

In an embodiment, a first loss contribution (a classification loss) may define a cross-entropy loss value for the classification branch (the object classification network) on its output layer, e.g. a softmax layer or the like. In an embodiment, the first loss contribution may be calculated as follows:

$$L_{cls} = \frac{1}{N_a} \sum_i p_i \cdot \log(p_i),$$

wherein $p_i$ may define the probability of a node of the 3D grid to be the center of a 3D anchor with an object (having a high IoU) and $p_i^*$ is its ground truth that is selected from the set $\{0,1\}$. The parameter Na defines the number of nodes of the 3D grid.

In an embodiment, a second loss contribution (a regression loss) may define a mean squared error at the output layer (preferably the linear output layer) of the regression branch (the object location predictor network). In an embodiment, the second loss contribution may be calculated as follows:

$$L_{reg} = \frac{1}{N_p} \sum_i \|t_i - t_i\|^2,$$

where $t_i$ may define the vector of three elements representing delta values of the central position or dimensions of the 3D anchors and $t_i^*$ is its ground truth. The parameter $N_p$ may define the number of positive anchors in the input IOS.

In an embodiment, a third loss contribution (a mask loss) may define a binary cross-entropy loss for classification of points (preferably all points) in positive anchors (preferably each positive anchor) at the output layer of the mask branch (the mask predictor network). The regression loss and mask loss may be taken into account only if a 3D anchor is labeled positive. The mask loss may be computed based on the following expression:

$$L_{mask} = \frac{1}{N_m} \sum_i p_i \cdot \log(p_i)$$

where $p_i$ is the probability that a point belongs to the corresponding object, encompassed by a 3D anchor. Here $p_i^*$ is the ground truth value from the set of $\{0,1\}$. The parameter N, may define the number of points inside the $i^{th}$ 3D anchor. During training, the regression loss and the mass loss may be used for changing the weights of the object location predictor network and the weights of the mask predictor network respectively.

In an exemplary embodiment of the training process of the system, a 3D anchor may be labeled positive if it has an overlap with any tooth instances in a labelled point cloud patch above a first threshold. In an embodiment, the first threshold may be 0.4 IoU, wherein IoU defines the average Jaccard Index. In another embodiment, a 3D anchor may be labeled negative if it has an overlap with any tooth instances in a labelled point cloud patch below a second threshold.

In an embodiment, the second threshold may be 0.2. Since the number of positive and negative 3D anchors are highly imbalanced, about 50% of each training batch may be selected from the positive 3D anchors and 25% from the negative 3D anchors. The rest of the 25% sampled 3D anchors in the training batch may be selected from the marginal 3D anchors, e.g. (0.2<IoU<0.4), which are considered also as negative samples.

Further, in an embodiment, during the training phase, the input to the Mask-MCNet may be randomly cropped patches of the point cloud. Each cropped patch may comprise a number of object instances, e.g. 2-4 tooth instances. In an embodiment, a uniform grid domain may be constructed. In another embodiment, a non-uniform grid domain may be constructed by filtering out nodes of a dense regular grid with 0.04 (lower bound) spatial resolution in each dimension. The upper bound for the grid resolution may be set to be equal to 0,12. In order to create sufficient overlap between 3D anchors and both small and large objects (e.g. incisor and molar teeth, respectively), 3D anchors of different dimensions may be used. For example, in an embodiment, two types (k=2) of 3D anchors boxes may be employed (with size of [0.3, 0.3, 0.2] and [0.15, 0.2, 0.2]).

FIGS. 12A and 128 depict flow-diagrams of training deep learning systems according to various embodiments of the invention. FIG. 12A depicts a flow-diagram of training a deep neural network system for object detection in a point cloud. The deep neural network may include a feature extraction network, an object proposal network and an object classification network according to any of the embodiments described in this application. As shown in the figure, in a first step (step 1202) a training point cloud sample comprising one or more labelled object instances may be provided to the input of a deep neural network system. The deep neural network system may include at least a feature extraction network, an object proposal network and an object classification network which are configured for object detection in a point cloud. A further step (step 1204) may include computing an object proposal by the object proposal network based on point cloud features determined by the feature extraction network. Here, an object proposal may define a 3D bounding box that may comprise points defining an object. Such 3D bounding box may be referred to as a 3D anchor. The training process may further include determining an overlap between the 3D anchor and a 3D bounding box of a labelled object instance in the training point cloud sample (step 1206). A 3D anchor may be labelled positive if the overlap is above a predetermined threshold and negative if the overlap is below a predetermined threshold. Next, an object prediction for a 3D anchor by the object classification network may be determined using the features in the 3D anchor (step 1208).

Thus, both positively and negatively labelled 3D anchors are used for the training of the object classification network. The object classification network may predict whether a 3D anchor should be labelled as positive (containing an object) or as negative (not containing an object). During training, in both cases the first loss function is used to determine a contribution (i.e. if the prediction was right the loss will be of value 0 (no correction), but if the prediction was wrong (negative prediction while it was positive or the other way around) then the loss value will be positive (and a correction of the network will be made)). The object prediction and a loss function may be used to obtain a loss value. Finally, the loss value may be used to train the feature extraction network, the object proposal network and the object classification network using a back-propagation method.

Figure 12B:
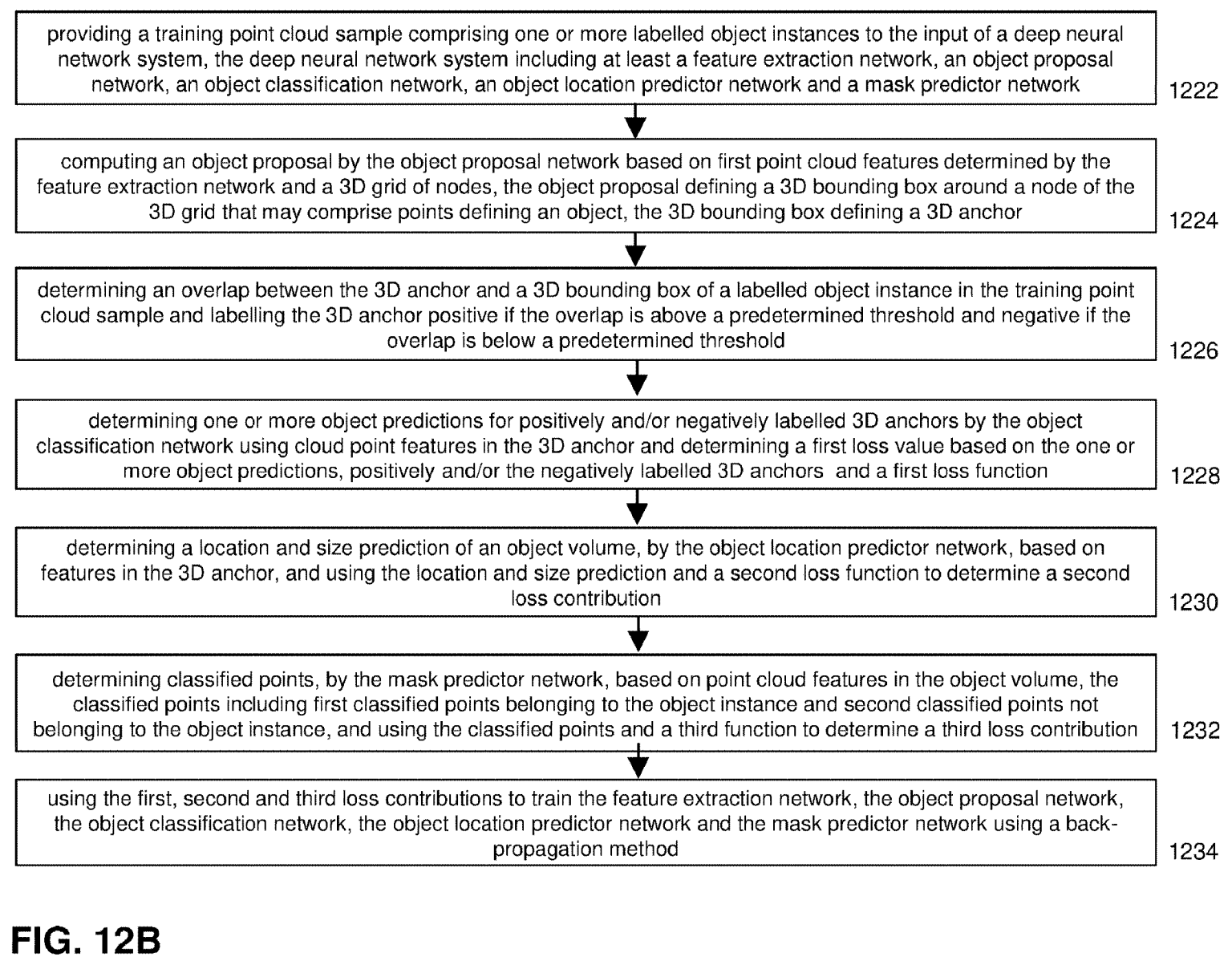

FIG. 12B depicts a flow-diagram of training a deep neural network system for instance segmentation of a point cloud according to an embodiment of the invention. In step step 1222 a training point cloud sample comprising one or more labelled object instances may be provided to the input of a deep neural network system. Here, the deep neural network system may be configured for instance segmentation of point clouds. Such network may include at least a feature extraction network, an object proposal network, an object classification network, an object location predictor network and a mask predictor network.

The training process may include computing an object proposal by the object proposal network based on point cloud features determined by the feature extraction network (step 1224), wherein an object proposal may define a 3D bounding box that may comprise points defining an object. Such 3D bounding box may define a 3D anchor. In a further step (step 1226) an overlap between the 3D anchor and a 3D bounding box of a labelled object instance in the training point cloud sample may be determined wherein the 3D anchor may be labelled positive if the overlap is above a predetermined threshold and negative if the overlap is below a predetermined threshold.

An object prediction may be determined, by the object classification network, for a positively or negatively labelled 3D anchor based on features in the 3D anchor (step 1228). The object classification network predicts whether a 3D anchor should be labelled as positive (containing an object) or as negative (not containing a (full) object). During training, in both cases the first loss function is used to determine a contribution (i.e. if the prediction was right the loss will be of value 0 (no correction), but if the prediction was wrong (negative prediction while it was positive or the other way around) then the loss value will be positive (and a correction of the network will be made)). This way, the difference between the object prediction and a ground truth (a labelled object) may be used to determine a first loss contribution based on a first loss function.

A location and size prediction of an object volume may be determined by the object location predictor network, based on the features in the 3D anchor (step 1230). Here, the object volume may be a 3D bounding box that has a center that should coincide with the center of the positively classified 3D anchor and that has dimensions that should closely match the dimensions of the object instance. A difference between the predicted location and size and a ground truth (a labelled location and size) may be used to determine a second loss contribution based on a second loss function. The larger the difference, the larger the loss contribution.

Classified points may be predicted by the mask predictor network based on first point cloud features in the object volume, the classified points may include first classified points belonging to the object instance and second classified points not belonging to the object instance. A difference between the predicted point classifications and a ground truth (labelled classified points) may be used to determine a third loss contribution based on a third function (step 1234). The first, second and third loss contributions may be used to train the feature extraction network, an object proposal network, an object classification network, an object location predictor network and a mask predictor network using a back-propagation method (step 1234).

Figure 13:
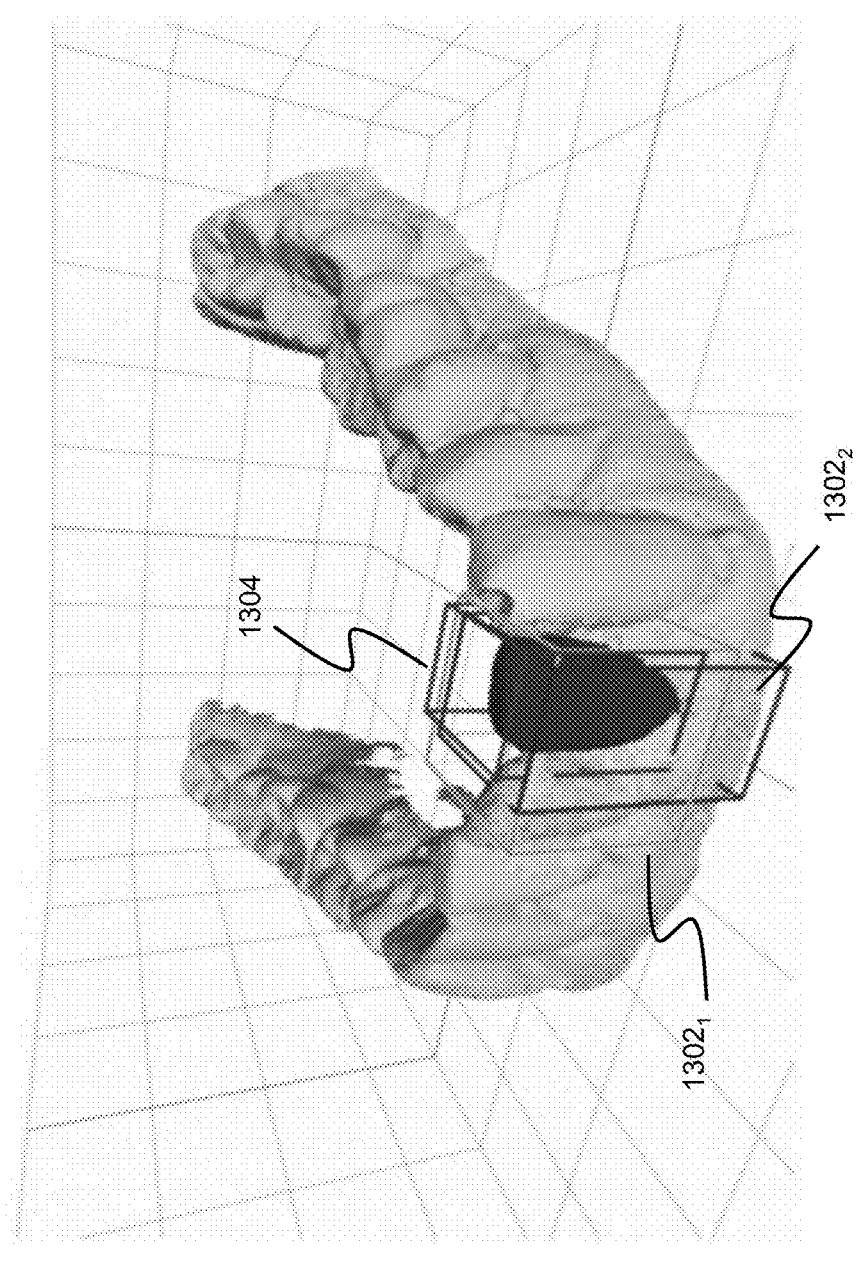
FIG. 13 depicts a visualization of positively classified 3D anchors determined by a Mask-MCNet according to an embodiment of the invention.

Inference on a new point cloud, e.g. a new IOS data set, may be performed by applying the Mask-MCNet on several cropped overlapping patches. Giving the 3D patches and applying a uniform 3D grid of nodes with the highest defined resolution (e.g. 0.04), the 3D anchors positioned on the nodes of the 3D grid are classified into object/no object by the classification branch. The dimensions and (central) positions of positively classified 3D anchors (i.e. object detected) are updated according to the estimated values by the regression branch (i.e. the object location predictor network). FIG. 13 depicts a visualization of positively classified 3D anchors $1302_{1,2}$ determined by the Mask-MCNet and a 3D bounding box $1302_{1,2}$ representing the ground truth. As shown in the figured, the two 3D anchors have different scales and central positions. The positively classified 3D anchors have an overlap with the ground truth 3D bounding box that is higher than the first threshold (in IoU) for labeling a 3D anchor as positive (i.e. containing (part of) an object).

Similar to Faster-RCNN, for each object, multiple 3D anchors may be detected, wherein each 3D anchor is associated with a probability score that is higher than the first threshold. Therefore, a non-maximum suppression algorithm may be employed according to the highest objectiveness scores (from classification probabilities). Hence, based on this algorithm a 3D anchor may be determined that has the highest probability score. The non-maximum suppression also handles the repeated points by overlapping the input patches. After predicting the bounding boxes of all tooth instances, retrieving a mask for all points inside the bounding box from the mask generation branch is straightforward.

Figure 14:
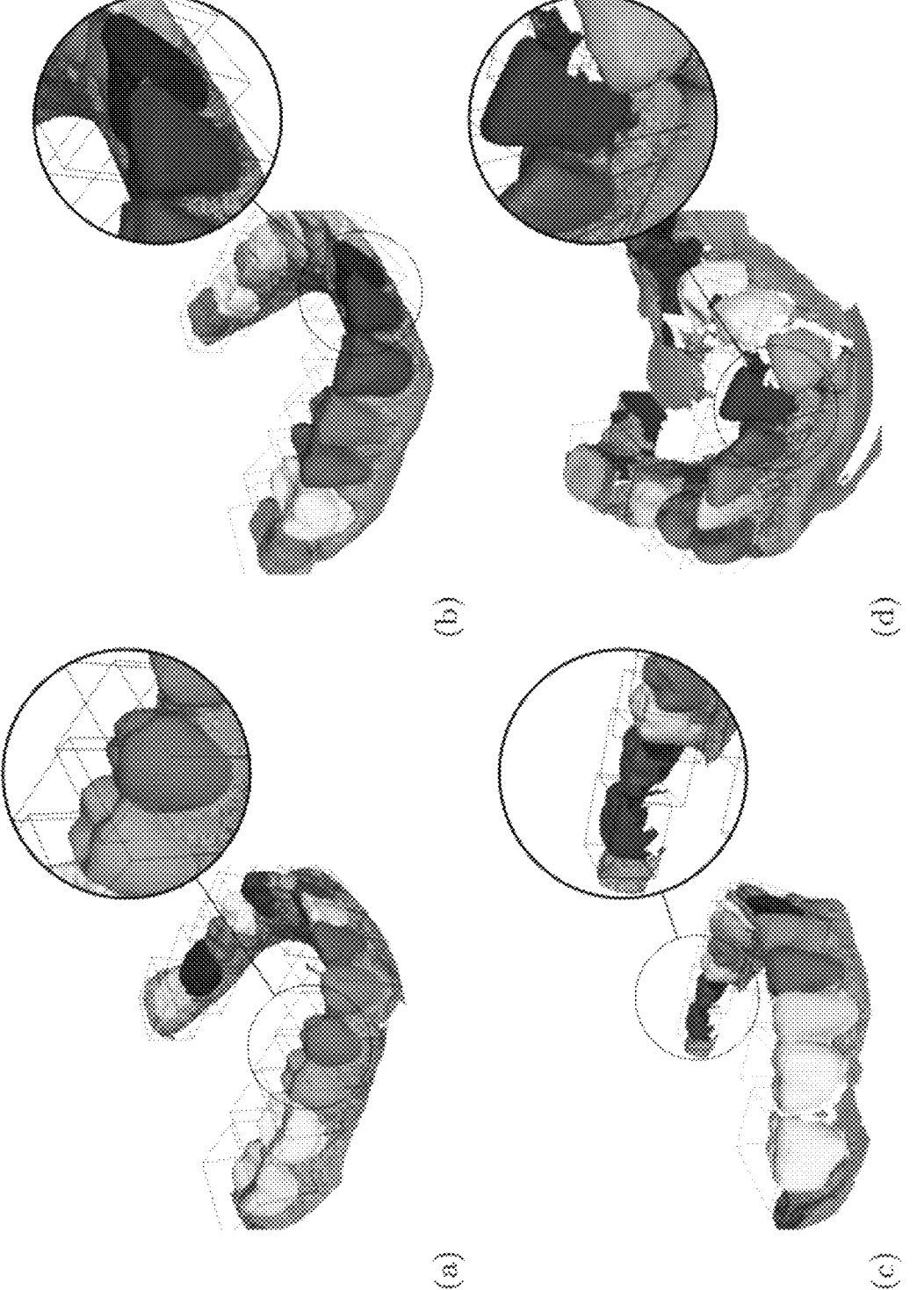
FIG. 14A-14H depicts examples of segmented IOS data generated by a deep learning system according to an embodiment of the invention.
Figure 14:
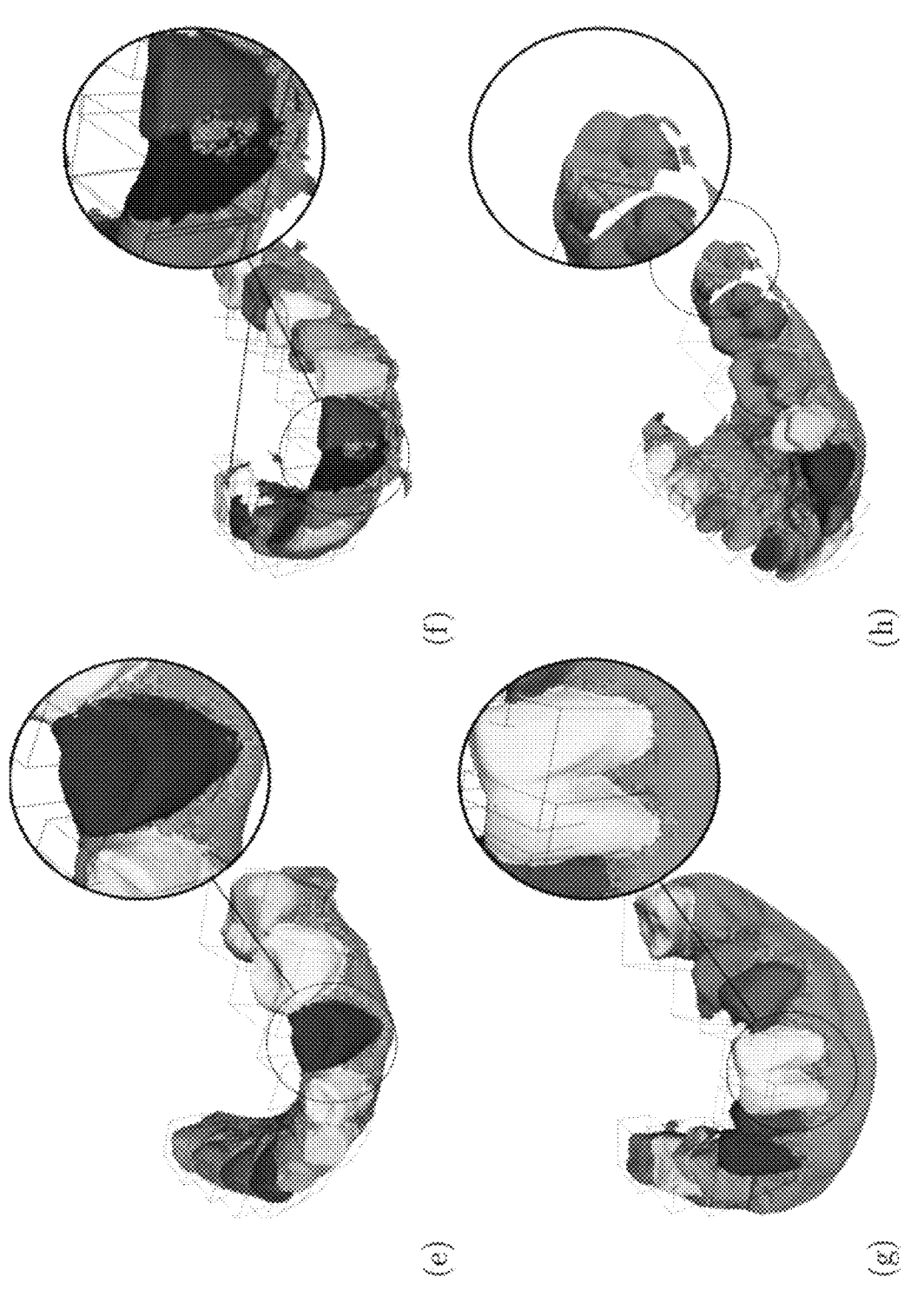

Examples of IOS instance segmentation by Mask-MCNet are visualized in FIG. 14A-14H. Here, FIG. 14A,B depicts segmentation of a normal dentition. FIG. 14C depicts a segmented dentition including segmented tooth having missing data. FIG. 14D-14F depict segmented dentitions including segmented tooth having abnormalities and artifacts. FIG. 14G,14H show two examples wherein the segmentation failed.

The performance of the Mask-MCNet in comparison with state-of-the-art classification networks is evaluated by five-fold cross-validation. The average Jaccard Index (also known as IoU) is used as a segmentation metric. Beside the IoU, the precision and recall for the multi-class segmentation problem is reported by treating each class individually (one-versus-all) as a binary problem. Additionally, the average scores are reported as well. The performance of the Mask-MCNet is shown in Table 1. As shown in Table 1, the proposed Mask-MCNet significantly outperforms state-of-the-art networks capable of segmenting point cloud data,

TABLE 1

| Method | Metric | | | Exec.time * |
| | IoU | Precision | Recall | (sec.) |
|---|---|---|---|---|
| PointNet [8] | 0.76 | 0.73 | 0.65 | 0.19 |
| PointGrid [4] | 0.80 | 0.75 | 0.70 | 0.88 |
| MCCNet [2] | 0.89 | 0.88 | 0.84 | 1.01 |
| PointCNN [5] | 0.88 | 0.87 | 0.83 | 0.66 |
| PointCNN++ [12] | 0.94 | 0.93 | 0.90 | 6.86 |
| Mask-MCNet (ours) | 0.98 | 0.98 | 0.97 | 14.6 |

* NVIDIA Titan-X GPU

Figure 15:
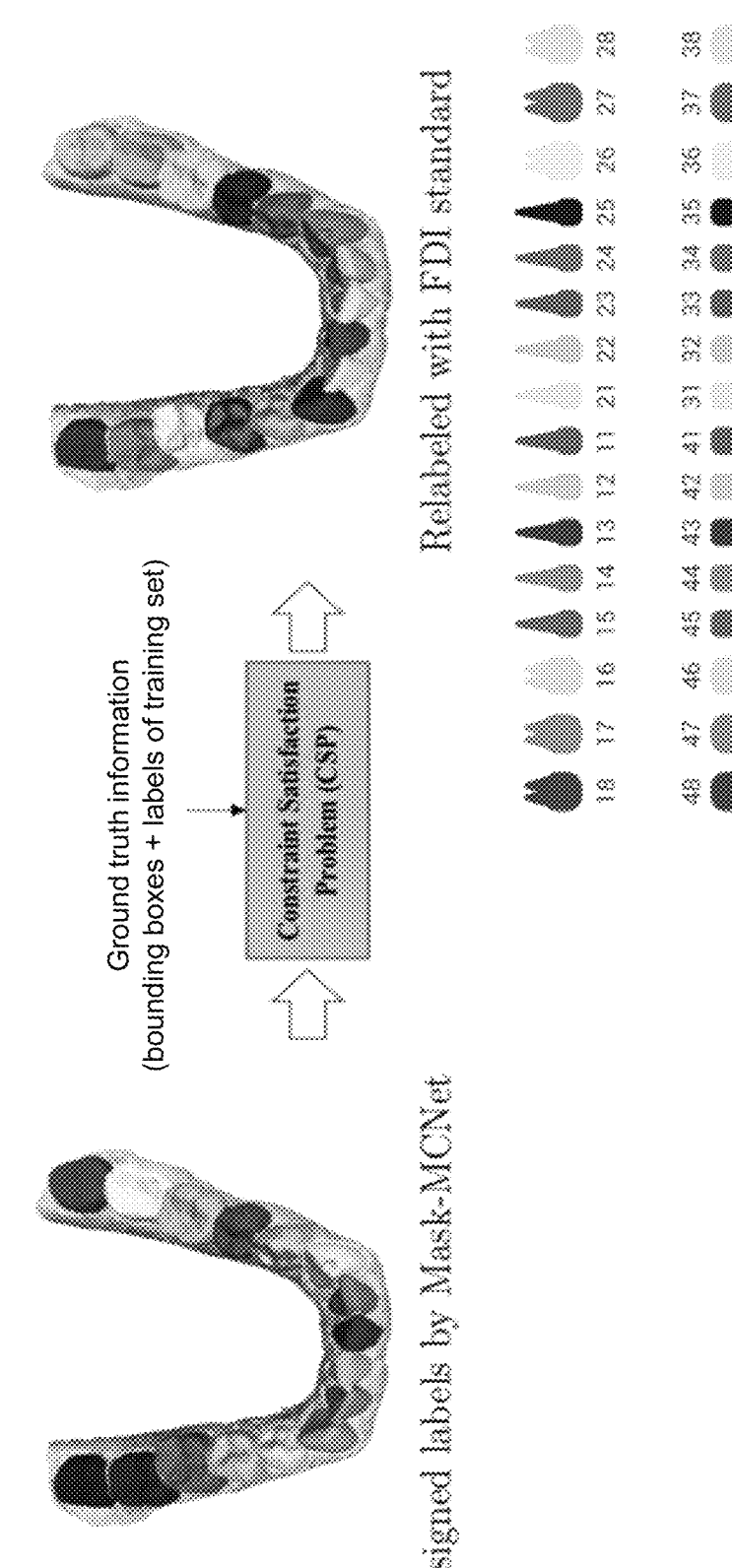
FIG. 15 depicts a flow-diagram of post-processing a segmented point cloud according to an embodiment of the invention.

FIG. 15 depicts a flow-diagram of post-processing a segmented point cloud according to an embodiment of the invention. For clinical purposes and consistency of the tooth labelling assignments, a post-processing method may be used for translating (via a look-up table) the instance labels predicted by the Mask-MCNet into FDI standard labels. By measuring the average central positions and sizes of the FDI labels within the training data, a combinatorial search algorithm may determine the most likely label assignment, which satisfies the predefined constraint (prior measurements on training data) in the context of a constraint satisfaction problem (CSP). Constraint satisfaction problems on finite domains are typically solved using a form of search. Techniques for such search may be variants of backtracking, constraint propagation or local search.

Figure 16:
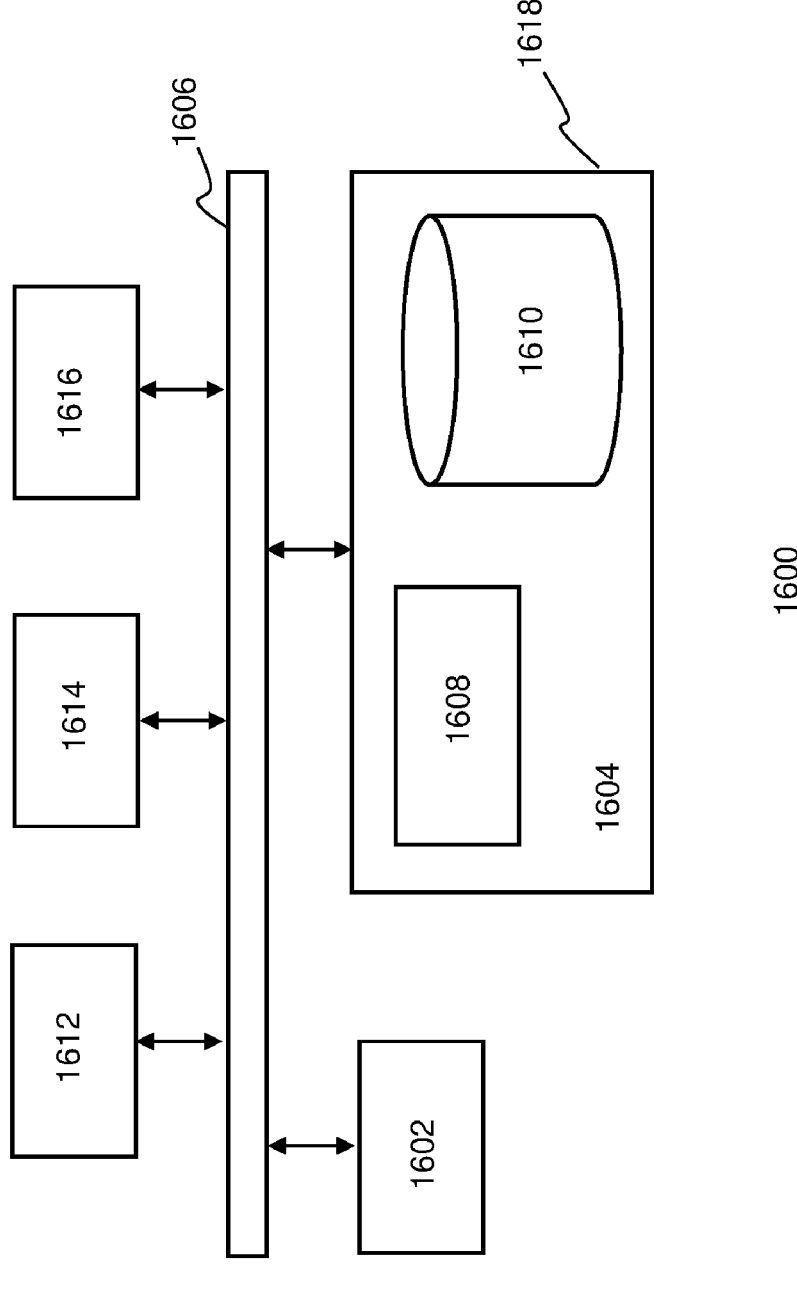
FIG. 16 is a block diagram illustrating an exemplary data processing system that may be used for executing methods and software products described in this application.

FIG. 16 is a block diagram illustrating an exemplary data processing system that may be used in embodiments as described in this disclosure. Data processing system 1600 may include at least one processor 1602 coupled to memory elements 1604 through a system bus 1606. As such, the data processing system may store program code within memory elements 1604. Furthermore, processor 1602 may execute the program code accessed from memory elements 1604 via system bus 1606. In one aspect, data processing system may be implemented as a computer that is suitable for storing and/or executing program code. It should be appreciated, however, that data processing system 1600 may be implemented in the form of any system including a processor and memory that is capable of performing the functions described within this specification.

Memory elements 1604 may include one or more physical memory devices such as, for example, local memory 1608 and one or more bulk storage devices 1610. Local memory may refer to random access memory or other non-persistent memory device(s) generally used during actual execution of the program code. A bulk storage device may be implemented as a hard drive or other persistent data storage device. The processing system 1300 may also include one or more cache memories (not shown) that provide temporary storage of at least some program code in order to reduce the number of times program code must be retrieved from bulk storage device 1610 during execution.

Input/output (I/O) devices depicted as input device 1612 and output device 1614 optionally can be coupled to the data processing system. Examples of input device may include, but are not limited to, for example, a keyboard, a pointing device such as a mouse, or the like. Examples of output device may include, but are not limited to, for example, a monitor or display, speakers, or the like. Input device and/or output device may be coupled to data processing system either directly or through intervening I/O controllers. A network adapter 1616 may also be coupled to data processing system to enable it to become coupled to other systems, computer systems, remote network devices, and/or remote storage devices through intervening private or public networks. The network adapter may comprise a data receiver for receiving data that is transmitted by said systems, devices and/or networks to said data and a data transmitter for transmitting data to said systems, devices and/or networks. Modems, cable modems, and Ethernet cards are examples of different types of network adapter that may be used with data processing system 1600.

As pictured in FIG. 16, memory elements 1604 may store an application 1618. It should be appreciated that data processing system 1600 may further execute an operating system (not shown) that can facilitate execution of the application. Application, being implemented in the form of executable program code, can be executed by data processing system 1600, e.g., by processor 1602. Responsive to executing application, data processing system may be configured to perform one or more operations to be described herein in further detail.

In one aspect, for example, data processing system 1600 may represent a client data processing system. In that case, application 1618 may represent a client application that, when executed, configures data processing system 1600 to perform the various functions described herein with reference to a "client". Examples of a client can include, but are not limited to, a personal computer, a portable computer, a mobile phone, or the like. In another aspect, data processing system may represent a server. For example, data processing system may represent a server, a cloud server or a system of (cloud) servers.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method of object detection in a point cloud generated by a 3D optical scanner, the method comprising:

determining by a first deep neural network, representing a feature extraction network, first features associated with points of the point cloud, the point cloud including points representing one or more objects representing one or more teeth in at least a 3D space of the point cloud, the first features defining geometrical information for each point of the point cloud, the first deep neural network being configured to receive points of the point cloud as input;

determining, by a second deep neural network representing an object proposal network, second features based on the first features and a uniform or non-uniform 3D grid of nodes in the space of the IOS point cloud; wherein the non-uniform 3D grid includes a dense distribution of nodes close to the surface of an object and a sparse distribution of nodes at distances further away from the surface of an object, the second features defining local geometrical information about the point cloud at positions of the nodes of the 3D grid in the 3D space of the point cloud;

generating one or more object proposals based on the second features, an object proposal defining a 3D bounding box positioned around a node of the 3D grid, the 3D bounding box containing points of the point cloud that may define a tooth, the 3D bounding box defining a 3D anchor;

determining, by a third deep neural network representing an object classification network, a score for the 3D anchor, the score indicating a probability that the 3D anchor includes points defining a tooth or part of a tooth, the determining being based on second features that are located in the 3D anchor.

2. The method according to claim 1 wherein the first features include first feature vectors, each first feature vector being associated with a point of the point cloud; and/or, the second features include second feature vectors, each second feature vector being associated with a node of the 3D grid.

3. The method according to claim 1 wherein the first deep neural network defines a feature extraction network configured to receive points of the point cloud and to generate the first features.

4. The method according to claim 3 wherein the first deep neural network includes a plurality of convolutional layers including multilayer perceptrons (MLPs), the feature extraction network being configured to receive points of a point cloud at its input and to generate a feature vector for each point of the point cloud at its output.

5. The method according to claim 3, wherein the feature extraction network includes one or more $\chi$-Conv layers, each $\chi$-Conv layer being configured to weigh and permute points and corresponding features provided to the input of the $\chi$-Conv layer and subsequently subjecting the permuted points and features to a convolution kernel comprising $\chi$-Conv layers.

6. The method according to claim 1 wherein the second type of deep neural network represents an object proposal network, the object proposal network including a plurality of convolutional layers, each of the plurality of convolutional layers including a multilayer perceptron (MLP) including one or more convolutional kernels.

7. The method according to claim 6, wherein the object proposal network is configured as a Monte Carlo Convolutional Network (MCCNet), comprising a plurality of Monte Carlo (MC) spatial convolutional layers.

8. The method according to claim 6, wherein the object proposal network is configured as a Monte Carlo Convolutional Network (MCCNet), comprising a plurality of Monte Carlo (MC) spatial convolutional layers, wherein each MC spatial convolutional layer comprising a convolutional kernel configured for determining a convolution at a location of a node x located in the 3D space of the point cloud.

9. The method according to claim 6, wherein the object proposal network is configured as a Monte Carlo Convolutional Network (MCCNet), comprising a plurality of Monte Carlo (MC) spatial convolutional layers, wherein each MC spatial convolutional layer comprising a convolutional kernel configured for determining a convolution at a location of a node x located in the 3D space of the point cloud, and wherein determining the convolution includes:

determining neighbouring points y within the receptive field r, the receptive field defining the field of view (FOV) of the convolutional kernel;

determining for each neighbouring point y a probability density function $p\,(x,y)$;

determining the convolution at a node based on a Monte Carlo estimation using the neighbouring points y and the probability density value $p\,(x,y)$ for each neighbouring point.

10. The method according to claim 1 wherein the third deep neural network represents an object classification network, the third deep neural network including a plurality of fully connected (FC) multilayer perceptron (MLP) layers, the second type of deep neural network being configured to receive features associated with a 3D anchor and to use the features to determine a score associated with the 3D anchor, the score indicating a probability that the 3D anchor includes points defining a tooth or part of a tooth.

11. Computer program product comprising software code portions configured for, when run in the memory of a computer, executing the method steps according to claim 1.

12. The method according to claim 1 wherein the first point cloud features include first feature vectors, each first feature vector being associated with a point of the point cloud, and wherein the first type of deep neural network defines a feature extraction network configured to receive points of the point cloud and to generate the first feature vectors associated with the points of the point cloud.

13. The method according to claim 1 wherein the second type of deep neural network represents an object proposal network, the object proposal network including a plurality of convolutional layers, each of the plurality of convolutional layers including a multilayer perceptron (MLP) including one or more convolutional kernels, and wherein at least one of the plurality of convolutional layers is configured to receive the first features and nodes of the uniform 3D grid and to determine the second features based on the first features.

14. A method of instance segmentation of a point cloud generated by a 3D optical scanner, the method comprising:

determining, by a first deep neural network representing a feature extraction network, first features associated with points of a point cloud, the point cloud including points representing one or more objects representing one of more teeth in a 3D space of the point cloud, the first features defining geometrical information for each point of the point cloud, the first deep neural network being configured to receive points of the point cloud as input;

determining, by a second deep neural network representing an object proposal network, second features based on the first features and a uniform or non-uniform 3D grid of nodes in the 3D space of the IOS point cloud, the second features defining local geometrical information about the point cloud at the position of the nodes of the 3D grid, in the 3D space of the IOS point cloud, wherein the non-uniform 3D grid includes a dense distribution of nodes close to the surface of an object and a sparse distribution of nodes at distances further away from the surface of an object;

generating object proposals based on the second features, an object proposal defining a 3D volume containing points that may define a tooth, the 3D volume of an object proposal defining a 3D anchor positioned around a node of the 3D grid;

determining a classified 3D anchor, by a third deep neural network representing an object classification network, the determining being based on a second feature set, the second feature set being a subset of the second features that are located in the 3D anchor;

determining an object volume, by a fourth deep neural network representing an object location predictor network, a centre position of the object volume coinciding with a centre location of an object instance and the dimensions of the object volume matching the outer dimensions of the object instance, the determining being based the second feature set; and, determining classified points, by a fifth deep neural network representing a mask predictor network, based on a set of points and a set of first point cloud features that are located in the object volume, the classified points including first classified points belonging to a tooth instance and second classified points not belonging to a tooth.

15. The method according to claim 14, wherein the first deep neural network defines a feature extraction network, the feature extraction network including a plurality of convolutional layers including multilayer perceptrons (MLPs), the feature extraction network being configured to receive points of a point cloud at its input and to generate a feature vector for each point of the point cloud at its output; and/or, wherein the second deep neural network represents an object proposal network, the object proposal network being configured as a Monte Carlo Convolutional Network (MCCNet) comprising a plurality of Monte Carlo (MC) spatial convolutional layers each layer including a multilayer perceptron (MLP) including one or more convolutional kernels; and/or, wherein the third deep neural network represents an object classification network, the third deep neural network including a plurality of fully connected (FC) multilayer perceptron (MLP) layers; and/or, wherein the fourth deep neural network represents an object location predictor network, the fourth deep neural network including a plurality of fully connected (FC) multilayer perceptron (MLP) layers; and/or, wherein the fifth deep neural network represents a mask predictor network, the fifth type of deep neural network including one or more χ-Conv layers, each χ-Conv layer being configured to weigh and permute points and corresponding features provided to the input of the χ-Conv layer and subsequently subjecting the permuted points and features to a convolution kernel.

16. The method according to claim 15 the object proposal network includes a plurality of convolutional layers, each layer including a multilayer perceptron (MLP) including one or more convolutional kernels, and wherein at least one of the plurality of convolutional layers is configured to receive the first point cloud features and nodes of the 3D grid and to transform the first point cloud features to the second point cloud features.

17. A computer system adapted to tooth detection in a point cloud generated by an 3D optical scanner, the system comprising:

a computer readable storage medium having computer readable program code embodied therewith, the program code including a pre-processing algorithm and at least a trained first 3D deep neural network, the computer readable program code; and a processor coupled to the computer readable storage medium, wherein responsive to executing the first computer readable program code, the processor is configured to perform executable operations comprising:

determining, by a first deep neural network representing a feature extraction network, first features associated with points of a point cloud, the point cloud including points representing one or more teeth in a 3D space of the point cloud, the first features defining geometrical information for each point of the point cloud, the first deep neural network being configured to receive points of the point cloud as input;

determining, by a second deep neural network representing a object proposal network, second features based on the first features, the second point cloud features defining local geometrical information about the point cloud at the position of nodes of a uniform or non-uniform 3D grid in the 3D space of the point cloud, wherein the non-uniform 3D grid includes a dense distribution of nodes close to the surface of an object and a sparse distribution of nodes at distances further away from the surface of an object;

generating one or more object proposals based on the second features, an object proposal defining a 3D bounding box positioned around a node of the 3D grid, the 3D bounding box containing points of the point cloud that may define a tooth, the 3D bounding box defining a 3D anchor;

determining, by a third deep neural network representing an object classification network, a score for the 3D anchor, the score indicating a probability that the 3D anchor includes points defining a tooth or part of a tooth, the determining being based on second features that are located in the 3D anchor.

18. A computer system adapted for instance segmentation of a point cloud generated by a 3D optical scanner, the system comprising:

a computer readable storage medium having computer readable program code embodied therewith, the program code including a pre-processing algorithm and at least a trained first 3D deep neural network, the computer readable program code; and a processor coupled to the computer readable storage medium, wherein responsive to executing the first computer readable program code, the processor is configured to perform executable operations comprising:

determining, by a first deep neural network representing a feature extraction network, first features associated with points of a point cloud, the point cloud including points representing one or more teeth in a 3D space of the point cloud, the first features defining geometrical information for each point of the point cloud, the first deep neural network being configured to receive points of the IOS point cloud as input;

determining, by a second deep neural network representing an object proposal network, second features based on the first features, the second features defining local geometrical information about the point cloud at the position of nodes of a uniform or non-uniform 3D grid spanning the 3D space of the point cloud, wherein the non-uniform 3D grid includes a dense distribution of nodes close to the surface of an object and a sparse distribution of nodes at distances further away from the surface of an object;

generating object proposals based on the second features, an object proposal defining a 3D volume containing points that may define a tooth, the 3D volume of an object proposal defining a 3D anchor positioned around a node of the 3D grid in the 3D space of the point cloud;

determining a classified 3D anchor, by a third deep neural network representing an object classification network, the determining being based on a second feature set, the second feature set being a subset of the second features that are located in the 3D anchor;

determining an object volume, by a fourth deep neural network representing an object location predictor network, a centre position of the object volume coinciding with a centre location of the object instance and the dimensions of the object volume matching the outer dimensions of the object instance, the determining being based the second feature set; and, determining classified points, by a fifth deep neural network representing a mask predictor network, based on a set of points and a set of first point cloud features that are located in the object volume, the classified points including first classified points belonging to a tooth and second classified points not belonging to a tooth.

* * * * *